US011040004B2

(12) United States Patent
Lebel

(10) Patent No.: US 11,040,004 B2
(45) Date of Patent: Jun. 22, 2021

(54) OTIC GEL FORMULATIONS FOR TREATING OTITIS EXTERNA

(71) Applicant: Otonomy, Inc., San Diego, CA (US)

(72) Inventor: Carl Lebel, Malibu, CA (US)

(73) Assignee: OTONOMY, INC., San Diego, CA (US)

( * ) Notice: Subject to any disclaimer, the term of this patent is extended or adjusted under 35 U.S.C. 154(b) by 59 days.

(21) Appl. No.: 15/705,101

(22) Filed: Sep. 14, 2017

(65) Prior Publication Data

US 2018/0085304 A1  Mar. 29, 2018

Related U.S. Application Data

(60) Provisional application No. 62/395,995, filed on Sep. 16, 2016.

(51) Int. Cl.
*A61K 9/00* (2006.01)
*A61K 9/06* (2006.01)
*A61K 31/496* (2006.01)
*A61K 47/10* (2017.01)
*A61K 31/133* (2006.01)

(52) U.S. Cl.
CPC .......... *A61K 9/0004* (2013.01); *A61K 9/0046* (2013.01); *A61K 9/06* (2013.01); *A61K 31/133* (2013.01); *A61K 31/496* (2013.01); *A61K 47/10* (2013.01); *Y02A 50/30* (2018.01)

(58) Field of Classification Search
CPC .. A61K 9/0046; A61K 31/496; A61K 9/0004; A61K 9/06; A61K 31/133; A61K 47/10
See application file for complete search history.

(56) References Cited

U.S. PATENT DOCUMENTS

| | | |
|---|---|---|
| 4,268,519 A | 5/1981 | Turner |
| 4,478,822 A | 10/1984 | Haslam et al. |
| 4,938,763 A | 7/1990 | Dunn et al. |
| 4,968,507 A | 11/1990 | Zentner et al. |
| 5,033,252 A | 7/1991 | Carter |
| 5,052,558 A | 10/1991 | Carter |
| 5,292,516 A | 3/1994 | Viegas et al. |
| 5,323,907 A | 6/1994 | Kalvelage |
| 5,324,519 A | 6/1994 | Dunn et al. |
| 5,401,741 A | 3/1995 | Sato et al. |
| 5,421,818 A | 6/1995 | Arenberg |
| 5,474,529 A | 12/1995 | Arenberg |
| 5,476,446 A | 12/1995 | Arenberg |
| 5,503,848 A | 4/1996 | Perbellini et al. |
| 5,702,716 A | 12/1997 | Dunn et al. |
| 5,744,153 A | 4/1998 | Yewey et al. |
| 5,861,174 A | 1/1999 | Stratton et al. |
| 5,990,194 A | 11/1999 | Dunn et al. |
| 6,004,573 A | 12/1999 | Rathi et al. |
| 6,045,528 A | 4/2000 | Arenberg et al. |
| 6,117,949 A | 9/2000 | Rathi et al. |
| 6,139,870 A | 10/2000 | Verrecchia |
| 6,177,434 B1 | 1/2001 | Kopke et al. |
| 6,201,065 B1 | 3/2001 | Pathak et al. |
| 6,201,072 B1 | 3/2001 | Rathi et al. |
| 6,284,804 B1 | 9/2001 | Singh et al. |
| 6,287,588 B1 | 9/2001 | Shih et al. |
| 6,359,016 B2 | 3/2002 | Singh et al. |
| 6,392,036 B1 | 5/2002 | Karlsson et al. |
| 6,488,952 B1 | 12/2002 | Kennedy et al. |
| 6,509,327 B1 | 1/2003 | Cagle et al. |
| 6,589,549 B2 | 7/2003 | Shih et al. |
| 6,649,621 B2 | 11/2003 | Kopke et al. |
| 6,740,664 B2 | 5/2004 | Cagle et al. |
| 7,001,615 B1 | 2/2006 | Singh et al. |
| 7,018,645 B1 | 3/2006 | Piao et al. |
| 7,524,834 B2 | 4/2009 | Karlsson et al. |
| 8,318,817 B2 | 11/2012 | Lichter et al. |
| 8,390,018 B2 | 3/2013 | Jang |
| 8,496,957 B2 | 7/2013 | Lichter et al. |
| 9,132,087 B2 | 9/2015 | Lichter et al. |
| 9,205,048 B2 | 12/2015 | Lichter et al. |
| 9,233,068 B2 | 1/2016 | Lichter et al. |
| 9,486,405 B2 | 11/2016 | Piu et al. |
| 9,603,796 B2 | 3/2017 | Lichter et al. |
| 2001/0034339 A1 | 10/2001 | Singh et al. |
| 2002/0022629 A1 | 2/2002 | Cagle et al. |
| 2002/0076441 A1 | 6/2002 | Shih et al. |
| 2002/0169142 A1 | 11/2002 | Jafari et al. |
| 2003/0092776 A1 | 5/2003 | Ron et al. |
| 2003/0229333 A1 | 12/2003 | Ashton et al. |
| 2004/0022853 A1 | 2/2004 | Ashton et al. |
| 2004/0082509 A1 | 4/2004 | Bonny |
| 2004/0101506 A1 | 5/2004 | Fust |
| 2004/0204471 A1 | 10/2004 | Seibert |
| 2005/0147585 A1 | 7/2005 | Schwarz |
| 2005/0159369 A1 | 7/2005 | Lane |
| 2005/0214338 A1 | 9/2005 | Guitton et al. |
| 2005/0287200 A1 | 12/2005 | Murthy et al. |
| 2006/0013858 A1 | 1/2006 | Trune |
| 2006/0034889 A1 | 2/2006 | Jo et al. |
| 2006/0046970 A1 | 3/2006 | Bowman et al. |
| 2006/0063802 A1 | 3/2006 | Guitton et al. |
| 2006/0264897 A1 | 11/2006 | Lobl et al. |
| 2006/0269602 A1 | 11/2006 | Dasch et al. |

(Continued)

FOREIGN PATENT DOCUMENTS

| | | |
|---|---|---|
| CN | 102112112 A | 6/2011 |
| EP | 0551626 A1 | 7/1993 |
| JP | H01258620 A | 10/1989 |
| JP | H04225914 A | 8/1992 |
| JP | H11500740 A | 1/1999 |

(Continued)

OTHER PUBLICATIONS

AAFP, AAO and AAP. Otitis Media with Effusion. Pediatrics 113(5):1412-1429 (2004).

(Continued)

*Primary Examiner* — Barbara P Badio
(74) *Attorney, Agent, or Firm* — Procopio, Cory, Hargreaves & Savitch LLP

(57) ABSTRACT

Disclosed herein are methods for the treatment of otic diseases or conditions with antimicrobial agent compositions and formulations administered locally to an individual afflicted with an otic disease or condition, through direct application of these compositions and formulations onto or via perfusion into the targeted auris structure(s).

17 Claims, 3 Drawing Sheets

(56) References Cited

U.S. PATENT DOCUMENTS

| | | |
|---|---|---|
| 2007/0048338 A1 | 3/2007 | Ladd |
| 2007/0110788 A1 | 5/2007 | Hissong et al. |
| 2007/0167918 A1 | 7/2007 | Reed et al. |
| 2008/0103118 A1 | 5/2008 | Clement et al. |
| 2008/0124385 A1 | 5/2008 | Campbell |
| 2008/0318918 A1 | 12/2008 | Campbell et al. |
| 2009/0156566 A1 | 6/2009 | Wall et al. |
| 2009/0246255 A1 | 10/2009 | Meyer |
| 2009/0297533 A1 | 12/2009 | Lichter et al. |
| 2009/0324552 A1 | 12/2009 | Lichter et al. |
| 2010/0015228 A1 | 1/2010 | Lichter et al. |
| 2010/0015263 A1 | 1/2010 | Lichter et al. |
| 2010/0036000 A1 | 2/2010 | Lichter et al. |
| 2010/0273864 A1 | 10/2010 | Lichter et al. |
| 2011/0166060 A1 | 7/2011 | Simons et al. |
| 2013/0178801 A1 | 7/2013 | Branch et al. |
| 2013/0216609 A1 | 8/2013 | Lichter et al. |
| 2015/0045739 A1 | 2/2015 | Nickel et al. |
| 2016/0000948 A1 | 1/2016 | Coleman et al. |
| 2016/0038594 A1 | 2/2016 | Lichter et al. |
| 2016/0067179 A1 | 3/2016 | Lichter et al. |
| 2017/0027930 A1 | 2/2017 | Piu et al. |

FOREIGN PATENT DOCUMENTS

| | | |
|---|---|---|
| JP | 2000514811 A | 11/2000 |
| JP | 2001520188 A | 10/2001 |
| JP | 2003510259 A | 3/2003 |
| JP | 2004507450 A | 3/2004 |
| JP | 2004536836 A | 12/2004 |
| JP | 2005504804 A | 2/2005 |
| JP | 2006097031 A | 4/2006 |
| JP | 2006111585 A | 4/2006 |
| JP | 2011528717 A | 11/2011 |
| JP | 2013508381 A | 3/2013 |
| WO | WO-9515152 A1 | 6/1995 |
| WO | WO-9738698 A1 | 10/1997 |
| WO | WO-9920261 A2 | 4/1999 |
| WO | WO-9924051 A2 | 5/1999 |
| WO | WO-9932151 A1 | 7/1999 |
| WO | WO-0007603 A2 | 2/2000 |
| WO | WO-0176558 A1 | 10/2001 |
| WO | WO-02056890 A1 | 7/2002 |
| WO | WO-03005961 A2 | 1/2003 |
| WO | WO-03017990 A2 | 3/2003 |
| WO | WO-03071986 A2 | 9/2003 |
| WO | WO-2004050021 A2 | 6/2004 |
| WO | WO-2006029074 A2 | 3/2006 |
| WO | WO-2006099325 A2 | 9/2006 |
| WO | WO-2007031098 A1 | 3/2007 |
| WO | WO-2007031280 A2 | 3/2007 |
| WO | WO-2007034989 A1 | 3/2007 |
| WO | WO-2007037874 A2 | 4/2007 |
| WO | WO-2007037886 A2 | 4/2007 |
| WO | WO-2007038949 A1 | 4/2007 |
| WO | WO-2008001341 A1 | 1/2008 |
| WO | WO-2008076556 A2 | 6/2008 |
| WO | WO-2009142719 A2 | 11/2009 |
| WO | WO-2015031393 A1 | 3/2015 |
| WO | WO-2018053173 A1 | 3/2018 |

OTHER PUBLICATIONS

Ahn et al. Lipoic acid rescues DBA mice from early-onset age-related hearing impairment. Neuroreport 19(13):1265-1269 (2008).
Ah-Tye et al. Otorrhea in Young Children After Tympanostomy-Tube Placement for Persistent Middle-Ear Effusion: Prevalence, Incidence, and Duration. Pediatrics 107(6):1251-1258 (2001).
Arnold et al. Novel slow- and fast-type drug release round-window microimplants for local drug application to the cochlea: an experimental study in guinea pigs. Audio! Neurootol 10(1):53-63 (2005).
Auris Medical. Press release reporting initiating of phase I/II clinical trial with AM-101. (1 pg.) (Feb. 22, 2007).
Auris Medical press release reporting results of phase I/II clinical trial with AM-111. (1 pg.)(Jun. 21, 2006).
Battaglia et al. Combination therapy (intratympanic dexamethasone + high-dose prednisone taper) for the treatment of idiopathic sudden sensorineural hearing loss. Otol Neurotol 29(4):453-460 (2008).
Bhoyar et al. A Noval Thermoreversible Phase transition System With Flux Enhancers for Opthalmic Application. Int J Pharm Pharm Sci. 3(4):367-370 (2011).
Bird et al. Intratympanic versus intravenous delivery of methylprednisolone to cochlear perilymph. Otology & Neurotology 28(8):1124-1130 (2007).
Bovo et al. Immune-mediated inner ear disease. Acta Oto-Laryngologica 126:1012-1021 (2006).
Campbell et al. Oral-D-methionine (MRX-1024) significantly protects against cisplatin-induced hearing loss: a phase II study in humans. Abst 32nd Ann MidWinter Res Meeting, ARO Abstracts 32:7 (Feb. 14-19, 2009).
Chen et al. Design and preparation of thermosensitive in situ gel of dexamethasone sodium phosphate. J Guangdong Coll Pharm 23(5):518-521 (2007) (English abstract).
Chen et al. Estrogen-related receptor beta/NR3B2 controls epithelial cell fate and endolymph production by the stria vascularis. Dev Cell 13(3):325-337 (2007).
Chen et al. Evaluation of thermosensitive in situ gel using dynamic rheological experiment, Chin Pharm J 43(6):444-447 (2008) (English abstract).
Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).
Chen et al. Preliminary study on brain-targeted drug delivery via inner ear. Acta Pharmaceutica Sinica 42:1102-1106 (2007) (English Abstract).
Chen et al. Preparation and characterization of dexamethasone acetate-loaded solid lipid nanoparticles. Chinese J Pharm 39(4):261-264 (2008) (English abstract).
Chen et al. Study on dexamethasone thermosensitive in situ gel for treating deafness. Chin Pharm J 41(9):685-688 (2006) (English abstract).
Ciprodex. product label 2009 (3 pgs.).
Co-pending U.S. Appl. No. 15/717,467, filed Sep. 27, 2017.
Dellamary et al. Assessing and optimizing osmolality of poloxamer 407 hydrogel formulations for sustained inner ear drug delivery. Poster. 2010 AAPS National Biotechnology Conference in San Francisco (1 pg.).
Dellamary et al. Development of poloxamer hydrogel formulations for sustained inner ear drug delivery. Poster. 2010 AAPS National Biotechnology Conference in San Francisco (1 pg.).
Dellamary et al. Novel poloxamer hydrogel formulations for sustained drug delivery to the middle ear. Abstract. 2010 Annual Meeting in New Orleans, Nov. 14-18 (1 pg.).
Dellamary et al. Novel poloxamer hydrogel formulations for sustained inner ear drug delivery. Abstract. Controlled Release Society 37th Annual Meeting and Exposition in Portland Jul. 10-14, 2010 (2 pgs.).
Derin et al. The effects of L-carnitine on presbyacusis in the rat model. Clin Otolaryngol Allied Sci 29(3):238-241(2004).
Dourmishev et al. Waardenburg syndrome. International Journal of Dermatology 38:656-663 (1999).
Dumortier et al. A Review of Poloxamer 407 Pharmaceutical and Pharmacological Characteristics. Pharm Res 23(12):2709-2728 (2006).
Elgen. Remington's Pharmaceuticals Sciences. 17th ed. pp. 1836-1837 (1985).
Endo et al. Novel strategy for treatment of inner ears using a biodegradable gel. Laryngoscope 115(11):2016-2020 (2005).
Fedder et al. Remington: The Science and Practice of Pharmacy. Lippincott Williams and Wilkins 21ed. pp. 1992-1993 (2005).
Feng et al. Effect of Poloxamer 407 on the cochlear orphology and hearing function after perfusion in round window: experiment with guinea pigs. National Medical Journal of China 87(32):2289-2291 (2007) (English Translation).

(56) References Cited

OTHER PUBLICATIONS

Feng et al. Effect of poloxamer 407 on the middle ear and inner ear after regional perfusion in guinea pigs. Zhonghua Er Bi Yan Hou Tou Jing Wai Ke Za Zhi 42(6):443-446 (2007) (English translation).

Fernandez et al. Self-curing controlled release systems for steroids. Application of prednisolone-based polymeric systems to ear diseases. Biomaterials 26(16):3311-3318 (2005).

Friedman et al. GRM7 variants confer susceptibility to age-related hearing impairment. Hum Mol Genet 18(4):785-796. (2009).

Garcia-Berrocal et al. Does the serological study for viral infection in autoimmune inner ear disease make sense? O.R.L. 70:16-20 (2008).

Gubbels et al. Functional auditory hair cells produced in the mammalian cochlea by in utero gene transfer. Nature 455(7212):537-541 (2008).

Guyot et al. Intratympanic application of an antiviral agent for the treatment of Meniere's disease. ORL J Otorhinolaryngol Relat Spec 70(1):21-6; discussion 26-27 (2008).

Hall et al. Anti-Pneumocystis activities of aromatic diamidoxime prodrugs. Antimicrobial Agents & Chemother. 42(3):666-674 (1998).

Hargunani et al. Intratympanic injection of dexamethasone: time course of inner ear distribution and conversion to its active form. Otol Neurotol 27(4):564-569 (2006).

Harris. Immunology of the inner ear: Response of the inner ear to antigen challenge. Otorhinolaryngology Head and Neck Surgery. 91:18-32 (1983).

Harris et al. Prevention of noise-induced hearing loss with Src-PTK inhibitors. Hear Res 208(1-2):14-25 (2005).

Harris et al. Treatment of corticosteroid-responsive autoimmune inner ear disease with methotrexate: a randomized controlled trial. JAMA 290(14):1875-1883 (2003).

Hill et al. Cisplation-Induced Ototoxicity: Effect of Intratympanic Dexamethasone Injections. Otol. Neurotol. 29(7):1005-1011 (2008).

Hoffer et al. Transtympanic management of tinnitus. Otolaryngol Clin North Am 36(2):353-358 (2003).

Hoshino et al. The non-steroidal anti-inflammatory drugs protect mouse cochlea against acoustic injury. Tohoku J Exp Med 216(1):53-59 (2008).

Inaoka et al. Local application of hepatocyte growth factor using gelatin hydrogels attenuates noise-induced hearing loss in guinea pigs. Acta Otolaryngol 129(4):453-457 (2009).

Jeong et al. Biodegradable block copolymers as injectable drug-delivery systems. Nature 388:860-862 (1997).

Jeong et al. Drug release from biodegradable injectable thermosensitive hydrogel of PEG-PLGA-PEG triblock copolymers. Journal of Controlled Release 63:155-163 (2000).

Jeong et al. Thermosensitive sol-gel reversible hydrogels. Advanced Drug Delivery Reviews 54:37-51 (2002).

Jia et al. Intratympanic dexamethasone for refractory sudden deafness. Lin Chung Er Bi Yan Hou Tou Jing Wai Ke Za Zhi 22(7):309-311 (2008) (English translation).

Karolewicz et al. Thermosensitive polymers in drug form technology H. Possibilities of use of thermosensitive polymers as active substance carriers. Polimery W Medycynie 38(1):15-26 (2008) (English abstract).

Keithley et al. GDNF protects the cochlea against noise damage. Neuroreport 9(10):2183-2187 (1998).

Khoo et al. Formulations for trans-tympanic antibiotic delivery. Biomaterials 34:1281-1288 (2013).

Kim et al. Effects of tumor necrosis factor alpha antagonist, platelet activating factor antagonist, and nitric oxide synthase inhibitor on experimental otitis media with effusion. Ann Otol Rhino! Laryngol 115(8):617-623 (2006).

Kitahara et al. Up-regulation of cochlear aquaporin-3 mRNA expression after intra-endolymphatic sac application of dexamethasone. Neurol Res. 25(8):865-870 (2003).

Lamm et al. The effect of prednisolone and non-steroidal anti-inflammatory agents on the normal and noise-damaged guinea pig inner ear. Hear Res 115(1-2):149-161 (1998).

Lavreysen et al. Therapeutic potential of group III metabotropic glutamate receptors. Curr Med Chem 15(7):671-84 (2008).

Lee et al. Novel therapy for hearing loss: delivery of insulin-like growth factor 1 to the cochlea using gelatin hydrogel. Otol Neurotol 28(7):976-981 (2007).

Lee et al. Regional delivery of vancomycin using pluronic F-127 to inhibit methicillin resistant *Staphylococcus aureus* (MRSA) growth in chronic otitis media in vitro and in vivo. J Control Release 96(1):1-7 (2004).

Lieberthal et al. The Diagnosis and Management of Acute Otitis Media. Pediatrics 131(3):e964-e999 (2013).

Liu et al. Permeability of different Dexamethasone drugs through round window membrane. Zhonghua Er Bi Yan Hou Tou Jing Wai Ke Za Zhi 41(3):211-215 (2006) (English abstract).

Lloyd et al. A patient with tinnitus. Clin Otolaryngology 33:25-28 (2008).

Majithiya et al. Thermoreversible-mucoadhesive Gel for Nasal Delivery of Sumatriptan. AAPS PharmSciTech 7(3):E1-E7 (2006).

McCarthy et al. Alport syndrome: a review. Clinical Eye and Vision Care 12:139-150 (2000).

McGuinness et al. Exogenous BDNF rescues rat spiral ganglion neurons in vivo. Otol Neurotol 26(5):1064-1072 (2005).

Meltser et al. Estrogen receptor beta protects against acoustic trauma in mice. J Clin Invest 118(4):1563-1570 (2008).

Miceli et al. Molecular pharmacology and therapeutic potential of neuronal Kv7-modulating drugs. Curr Opin Pharmacol 8(1):65-74 (2008).

Mitsukawa et al. A selective metabotropic glutamate receptor 7 agonist: activation of receptor signaling via an allosteric site modulates stress parameters in vivo. PNAS USA 102(51):18712-18717 (2005).

Morden et al. Topical Fluoroquinolones for Eye and Ear. Am Fam Physician 62(8):1870-1876 (2000).

Mostafa Transtympanic Membrane Delivery of Antibiotics-Pharmacokinetic Studies in Chinchillas. Dissertation submitted to the Graduate School of the University of Minnesota in (Mar. 2007).

Nakagawa et al. Local drug delivery to inner ear for treatment of hearing loss. Curr Drug Ther 3:143-147 (2008).

Nance et al. The Genetics of Deafness. Mental Retardation and Developmental Disabilities 9:109-119 (2003).

Nishimaki et al. Reduction of metabotropic glutamate receptor-mediated heterosynaptic inhibition of developing MNTB-LSO inhibitory synapses. Eur J Neurosci 26(2):323-330 (2007).

Nouvian et al. Degeneration of sensory outer hair cells following pharmacological blockade of cochlear KCNQ channels in the adult guinea pig. Eur J Neurosci 17(12):2553-2562 (2003).

Oldstone. Virus-induced autoimmunity: molecular mimicry as a route to autoimmune disease. J. Autoimmune 2(suppl):187-194 (1989).

Oliveira et al. Viral etiology for inner ear diseases: proven, unproven, unlikely. ORL 70:42-51 (2008).

Pappas et al. Topical Antibiotic Ear Drops: Are They Safe? Int J Clin Pract. 60:1115-1119 (2006).

Park et al. Effect of inhibitor of tumor necrosis factor-alpha and oxatomide on immune mediated otitis media. Laryngoscope 116(9):1642-1646 (2006).

Parnes et al. Corticosteroid pharmacokinetics in the inner ear fluids: an animal study followed by clinical application. Laryngoscope 109(7 Pt 2 Supplement No. 91):1-17 (1999).

PCT/US2009/051172 International Search report dated Feb. 18, 2010.

PCT/US2014/052754 International Preliminary Report on Patentability dated Mar. 10, 2016.

PCT/US2014/52754 International Search Report and Written Opinion dated Nov. 4, 2014.

Pelton et al. Recent Advances in Otitis Media. Pediatric Infectious Disease Journal 28(10):5133-5137 (2009).

Peng et al. Clinical investigation of different routes of administration of dexamethasone on sudden deafness. Lin Chung Er Bi Yan Hou Tou Jing Wai Ke Za Zhi 22(10):442-445. (2008) (English translation).

(56) References Cited

OTHER PUBLICATIONS

Piu et al. OTO-104: A Sustained-Release Dexamethasone Hydrogel for the Treatment of Otic Disorders. Otol & Neurology 32(1):171-179 (2011).
Piu et al. OTO-104: A Sustained-Release Dexamethasone Hydrogel formulation for the treatment of Meniere's disease, Oral Presentation title: Recent Topics in Meniere's disease treatment, Nov. 16, 2010 (1 pg.).
Piu et al. Towards predicting human inner ear pharmacokinetics: allometric scaling using guinea pigs and sheep. Abstract. ARO Meeting, Feb. 6-10, 2010 (1 pg).
Plontke et al. Rapid clearance of methylprednisolone after intratympanic application in humans. Comment on: Bird PA. Begg EJ. Zhang M. et al. Intratympanic versus intravenous delivery of methylprednisolone to cochlear perilymph. Otol Neurotol (2007); 28:1124-30. Otol Neurotol 29(5):732-733 (2008).
Pondugula et al. Glucocorticoid regulation of genes in the amiloride-sensitive sodium transport pathway by semicircular canal duct epithelium of neonatal rat. Physiol Genomics 24(2):114-123 (2006).
Pondugula et al. Glucocorticoids stimulate cation absorption by semicircular canal duct epithelium via epithelial sodium channel. Am J Physiol Renal Physiol 286(6):F1127-1135 (2004).
Psillas et al. Potential efficacy of early treatment of acute acoustic trauma with steroids and piracetam after gunshot noise. Eur Arch Otorhinolaryngol 265(12):1465-1469 (2008).
Puel. Chemical synaptic transmission in the cochlea. Prog Neurobiol 47(6):449-476 (1995).
Richard et al. Effects of sterilizing-grade filters on the physico-chemical properties of onion-like vesicles. Int J Pharm 312(1-2):144-150 (2006).
Roland et al. Microbiology of Acute Otitis Media With Tympanostomy Tubes. Otolaryngology—Head and Neck Surgery 133(4):585-595 (2005).
Ross et al. Aqueous Solubilities of some variously Substituted Quinoline Antimicrobials. Int'l J of Pharm 63:237-250 (1990).
Salt et al. Distribution of Dexamethasone and Preservation of Inner Ear Function following Intratympanic Delivery of a Gel-Based Formulation. Audiology Neurology 16:323-335 (2011).
Satoh et al. Tumor necrosis factor-alpha, an initiator, and etanercept, an inhibitor of cochlear inflammation. Laryngoscope 112:1627-1634 (2002).
Schoepp et al. Pharmacological agents acting at subtypes of metabotropic glutamate receptors. Neuropharmacology 38(10):1431-1476 (1999).
Schuknecht. Ablation therapy for the relief of Ménière's disease. Laryngoscope 66:859-870 (1956).
Seidman et al. Anti-intercellular adhesion molecule-1 antibody's effect on noise damage. Laryngoscope 119(4):707-712 (2009).
Shaikh et al. How do parents of preverbal children with acute otitis media determine how much ear pain their child is having? The Journal of Pain 11(12):1291-1294 (2010).
She et al. A short term study on the efficacies of intratympanic prednisolone and dexamethasone injection for subjective tinnitus. Lin Chung Er Bi Yan Hou Tou Jing Wai Ke Za Zhi 22(19):871-873 (2008) (English translation).
Shepherd et al. Neurotrophins and electrical stimulation for protection and repair of spiral ganglion neurons following sensorineural hearing loss. Hear Res 242(1-2):100-109 (2008).
Shinohara et al. Neurotrophic factor intervention restores auditory function in deafened animals. PNAS USA 99(3):1657-1660 (2002).
Sismanis. Tinnitus. Curr Neurol Neurosci Rep. 1(5):492-499 (2001).
Song. Design and Synthesis of Factor Xa Inhibitors and their Prodrugs. Bioorganic & Medicinal Chemistry Letters 13:297-300 (2003).
Sun et al. In vitro permeability of round window membrane to transforming dexamethasone with delivery vehicles—a dosage estimation. Chin Med J 120(24):2284-2289 (2007) (English translation).
Synphora AB. website printout for JB004/A 2009 (1 pg.).
Tabuchi et al. Hearing impairment in TRPV4 knockout mice. Neurosci Lett 382(3):304-308 (2005).

Taguchi et al. Expressions of aquaporin-2. vasopressin type 2 receptor. transient receptor potential channel vanilloid (TRPV)1. and TRPV4 in the human endolymphatic sac. Laryngoscope 117(4):695-698 (2007).
Tahera et al. NF-kB mediated glucocorticoid response in the inner ear after acoustic trauma. J Neurosci Res 83(6):1066-1076 (2006).
Takeda et al. Aquaporins as potential drug targets for Meniere's disease and its related diseases. Handb Exp Pharmacol 190:171-184 (2009).
Takeda et al. Decompression effects of erythritol on endolymphatic hydrops. Auris Nasus Larynx 36(2):146-151 (2009).
Takeda et al. The effects of V2 antagonist (OPC-31260) on endolymphatic hydrops. Hear Res 182(1-2):9-18. (2003).
Takemura et al. Direct inner ear infusion of dexamethasone attenuates noise-induced trauma in guinea pig. Hear Res 196(1-2):58-68 (2004).
Taktak et al. Assay of Pyrogens by Interleukin-6 Release from Monocytic Cell Lines. J. Pharm. Pharmacol. 43:578-582 (1991).
Takumida et al. Nitric oxide in the inner ear. Cur Opin Neurol 15(1):11-15 (2002).
Tang et al. COUP-TFI controls Notch regulation of hair cell and support cell differentiation. Development 133(18):3683-3693 (2006).
The Royal National Institute for Deaf People (RNID) advertisement insert in Nature Reviews Drug Discovery, May 2009 (4 pgs.).
The U. S. Food and Drug Administration has provided regulatory guidance in the publication: Guidance for Industry: Sterile Drug Products Produced by Aseptic Processing. available at: http://www.fda.gov/cder/guidance/5882fn1.htm (Aug. 2003) (63 pgs.).
Thorne et al. Potential role of purinergic signalling in cochlear pathology. Audiol Neurootol 7(3):180-184 (2002).
U.S. Appl. No. 13/645,126 Office Action dated Jan. 22, 2015.
U.S. Appl. No. 13/645,126 Office Action dated Jun. 12, 2015.
U.S. Appl. No. 13/848,636 Office Action dated May 14, 2015.
U.S. Appl. No. 14/469,408 Office Action dated May 6, 2016.
U.S. Appl. No. 14/469,408 Office Action dated Oct. 7, 2015.
U.S. Appl. No. 14/618,926 Office Action dated Mar. 24, 2015.
U.S. Appl. No. 14/618,926 Office Action dated May 4, 2015.
U.S. Appl. No. 14/741,092 Office Action dated May 31, 2016.
U.S. Appl. No. 14/741,092 Office Action dated Nov. 14, 2016.
U.S. Appl. No. 14/836,184 Office Action dated Oct. 13, 2016.
U.S. Appl. No. 14/922,448 Office Action dated Apr. 15, 2016.
U.S. Appl. No. 15/264,107 Office Action dated Jan. 6, 2017.
U.S. Appl. No. 15/264,107 Office Action dated Sep. 8, 2017.
Van Wijk et al. Local perfusion of the tumor necrosis factor alpha blocker infliximab to the inner ear improves autoimmune neurosensory hearing loss. Audiol Neurootol 11(6):357-365 (2006).
Viegas et al. Osmotic behavior of poloxamer 407 and other non-ionic surfactants in aqueous solutions. Int. J. Pharm. 160:157-162 (1998).
Wang et al. A novel dual inhibitor of calpains and lipid peroxidation (BN82270) rescues the cochlea from sound trauma. Neuropharmacology 52(6):1426-1437 (2007).
Wang et al. Dose-dependent sustained release of dexamethasone in inner ear cochlear fluids using a novel local delivery approach. Audiol Neurotol 14:393-401 (2009).
Wang et al. Over-expression of X-linked inhibitor of apoptosis protein slows presbycusis in C57BL/6J mice. Neurobiol Aging 12 pgs. (2008).
Wang et al. Pharmacokinetic and safety profile of OTO-104: a sustained release dexamethasone hydrogel for inner ear delivery. Abstract. ARO Meeting, Feb. 6-10, 2010 (1 pg.).
Wang et al. Pharmacokinetic and toxicity profile of the clinical candidate OTO-104: a sustained release dexamethasone hydrogel for inner ear delivery. 2010 Abstracts selected for AOS spring meeting. Las Vegas, NV. May 1-2, 2010 (2 pgs.).
Wang et al. Pharmacokinetic and toxicity profile of the clinical candidate OTO-104: a sustained release dexamethasone hydrogel for inner ear delivery. Abstract. COSM Meeting, May 1-2, 2010 (2 pgs.).
Wang et al. Pharmacokinetic and Toxicity Profile OTO-104: A Sustained Release Dexamethasone Hydrogel for Inner Ear Delivery. Abstract 644. Section: Q8. Feb. 8, 2010 (2 pgs.).

(56) References Cited

OTHER PUBLICATIONS

Wang et al. Pharmacokinetics of dexamethasone solution following intratympanic injection in guinea pig and sheep. Audiol Neurotol 16:233-241 (2011).
Wang et al. Principles of Inner Ear Sustained Release Following Intratympanic Administration, Laryngoscope 121:385-391 (2011).
Watanabe et al. Inhibition of inducible nitric oxide synthase lowers the cochlear damage by lipopolysaccharide in guinea pigs. Free Radic Res 32(4):363-370. (2000).
Watanabe et al. Nitric oxide synthase inhibitor reduces the apoptotic change in the cisplatin-treated cochlea of guinea pigs. Anticancer Drugs 11(9):731-735 (2000).
Watanabe et al. Nitric oxide synthase inhibitor suppresses the ototoxic side effect of cisplatin in guinea pigs. Anticancer Drugs 11(5):401-406. (2000).
Yamamoto et al. Inhibition of Notch/RBP-J signaling induces hair cell formation in neonate mouse cochleas. J Mol Med 84(1):37-45 (2006).
Yang et al. Intratympanic immunosuppressives for prevention of inunune-mediated sensorineural hearing loss. Am J Otol 21(4):499-504 (2000).
Yildirim et al. Effect of intratympanic dexamethasone on noise-induced temporary threshold shift. Laryngoscope 115(7):1219-1222 (2005).
Zheng et al. Vanilloid receptors in hearing: altered cochlear sensitivity by vanilloids and expression of TRPV1 in the organ of corti. J Neurophysiol 90(1):444-455 (2003).
Zhou et al. Intratympanic administration of methylprednisolone reduces impact of experimental intensive impulse noise trauma on hearing. Acta Oto-Laryngologica 129:602-607 (2009).
Co-pending U.S. Appl. No. 15/710,727, filed Sep. 20, 2017.
External Acoustic Meatus Dec. 27, 2015 BodyMaps (2 pgs.).
PCT/US2017/051625 International Search Report and Written Opinion dated Jan. 2, 2018.
PCT/US2017/053715 International Search Report and Written Opinion dated Nov. 22, 2017.
Dohar. Tympanostomy Tubes: Not the Magic Bullet for Acute Otitis Media. Medscape (https://medscape.org/viewarticle/730700_print) (9 pgs) (2010).
U.S. Appl. No. 15/264,107 Office Action dated Nov. 2, 2018.
U.S. Appl. No. 15/710,727 Office Action dated May 1, 2019.
U.S. Appl. No. 15/710,727 Office Action dated Sep. 24, 2018.
U.S. Appl. No. 15/717,467 Office Action dated Sep. 24, 2018.
WebMD. What is Swimmer's Ear? © 2018. Accessed Sep. 29, 2018. Available from:< https://www.webmd.com/cold-and-flu/ear-infection/understanding-swimmer-ear-basics#1 (6 pgs) (2018).
Salt et al. "Local inner-ear drug delivery and pharmacokinetics." Drug Discovery Today. 10(19)1299-1306 (Oct. 1, 2005).
Extended European Search Report for related EP Patent Application No. 17851549.0, dated Mar. 13, 2020, in 8 pages.

OTIC GEL FORMULATIONS FOR TREATING OTITIS EXTERNA

CROSS REFERENCE

This application claims the benefit of U.S. Provisional Application No. 62/395,995, filed Sep. 16, 2016, which application is incorporated herein by reference in its entirety.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

Diseases of the external auditory canal (also referred to as aurus externa and external ear) have to date been treated with solutions applied in the form of drops. Drops have limited residence time and require multiple daily applications for 7-10 days. Compliance and accurate delivery are challenging for both adults that self-administer, as well as caregivers that are treating children with diseased ears.

SUMMARY OF THE INVENTION

Disclosed herein are methods of treating otitis externa comprising administering into an ear canal, of an ear of a subject in need thereof, an aqueous thermoreversible gel composition comprising about 6.0% by weight of micronized ciprofloxacin and 15-17% by weight of poloxamer 407. In some embodiments, the composition comprises from about 6 mg to about 24 mg by weight of micronized ciprofloxacin. In some embodiments, the composition comprises from about 10 mg to about 15 mg by weight of micronized ciprofloxacin. In some the composition comprises about 12 mg by weight of micronized ciprofloxacin. In some embodiments, the methods comprise administering about 0.1 mL to 1.0 mL volume of the aqueous thermoreversible gel composition in a single administration. In some embodiments, the methods comprise administering about 0.2 mL to 0.5 mL volume of the aqueous thermoreversible gel composition in a single administration. In some embodiments, the methods comprise administering about 0.2 mL of the aqueous thermoreversible gel composition containing about 12 mg by weight of micronized ciprofloxacin. In some embodiments, the composition is free of butylated hydroxytoluene (BHT). In some embodiments, the composition is preservative-free. In some embodiments, the composition further comprises tromethamine. In some embodiments, the composition has a pH of about 7.0 to about 8.0. In some embodiments, the otitis externa is associated with a bacterial infection. In some embodiments, the bacterial infection is associated with *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof. In some embodiments, the otitis externa is acute otitis externa. In some embodiments, the subject has experienced a symptom of acute otitis externa for less than six weeks, wherein the symptom is selected from decreased hearing, swelling of the ear canal, ear pain, fever, exudate from the ear canal, and combinations thereof. In some embodiments, the administering comprises contacting the ear canal with a tip of a syringe containing the aqueous thermoreversible gel composition. In some embodiments, the tip of the syringe is advanced about 1 mm to about 8 mm beyond the cartilaginous/bony junction of the ear. In some embodiments, the tip of the syringe is advanced about 5 mm beyond the cartilaginous/bony junction of the ear.

DETAILED DESCRIPTION OF THE INVENTION

Figure 1:
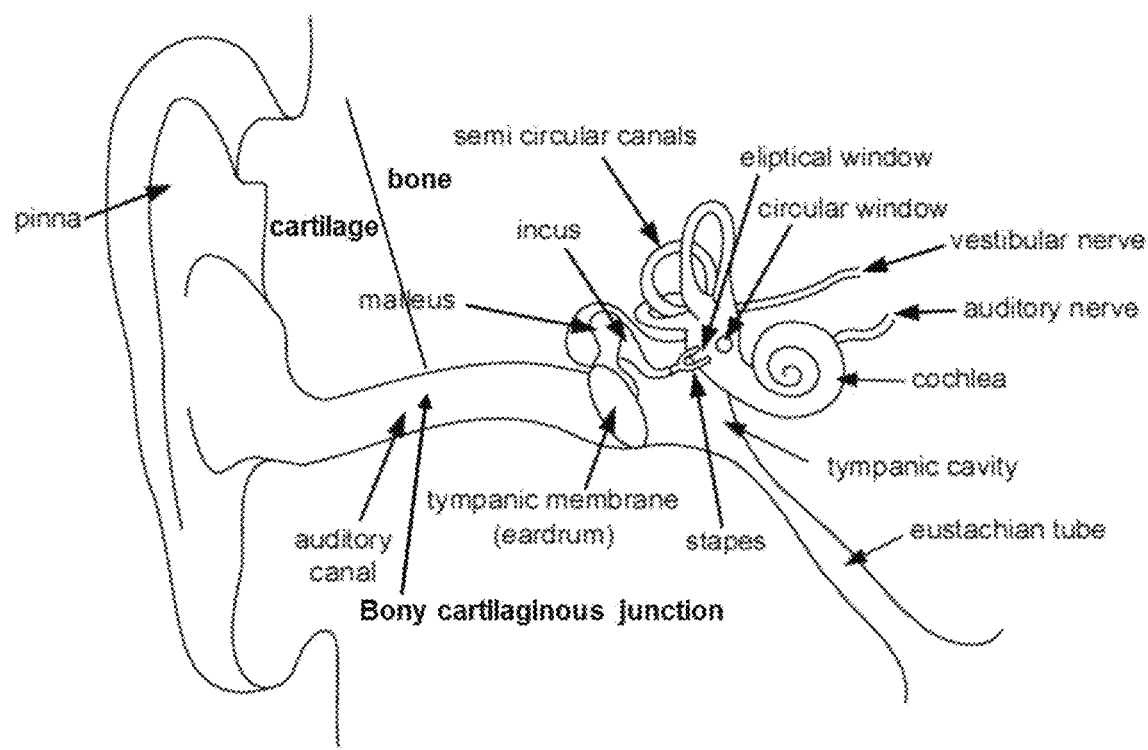
FIG. 1 illustrates the anatomy of the ear.

Provided herein are controlled release antimicrobial agent compositions and formulations suitable for local administration to the external auditory canal (EAC) of the ear. In some embodiments, the antimicrobial agent is ciprofloxacin. Compositions comprising combinations of therapeutic agents useful for the treatment of otic disorders, including combinations of different antimicrobial agents, as well as combinations of antimicrobial agents with other therapeutic agents, are also encompassed in certain embodiments disclosed herein.

Otitis externa (OE), also referred to as swimmer's ear, is an inflammation of the external ear and/or ear canal. OE is primarily caused by bacteria (e.g., *Pseudomonas aeruginosa* and *Staphylococcus aureus*) or fungi (e.g., *Candida albicans* and *Aspergillus*) in the outer ear, which establish infection following damage to the skin of the ear canal. Symptoms of OE include otalgia, swelling, and otorrhea. If the condition progresses significantly, OE may cause temporary conductive hearing loss as a result of the swelling and discharge. Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids.

Systemic antimicrobial administration for the treatment of otic disorders, e.g., OE, OM and otosyphilis, may create a potential inequality in drug concentration with higher circulating levels in the serum, and lower levels in the target auris interna organ structures. As a result, fairly large amounts of drug are required to overcome this inequality in order to deliver sufficient, therapeutically effective quantities to the outer ear. Further, bioavailability is often decreased due to metabolism of the drug by the liver. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant undesired side effects of systemic delivery of antimicrobial agents (which are generally understood to be toxic to cells), disclosed herein are methods and compositions for local delivery of antimicrobial agents to auris externa structures. In some embodiments, the auris-acceptable sustained-release formulations disclosed herein are capable of being administered into the external ear canal. In some embodiments, the formulations disclosed herein are administered with a syringe (without needle), a dropper, or a catheter. Administration to the outer ear or external ear canal generally does not comprise injection or use of a needle.

Because of the localized targeting of the antimicrobial agent formulations and compositions, the risk of adverse effects can be reduced as a result of treatment with previously characterized toxic or ineffective antimicrobial agent. Localized administration of antimicrobial agent compositions reduces the risk of development of resistance to antibiotics compared to the risk for development of antibiotic resistance when an antibiotic is administered systemically. The compositions described herein are effective for recurring otic diseases or conditions including, for example, recurring ear infections in children without the need for changing treatment regimens (e.g., in response to development of antibiotic resistance). Accordingly, also contemplated within the scope of the embodiments herein is the use of antimicrobial agents in the treatment of otic diseases or conditions including otitis externa, including therapeutic agents that have been previously rejected by practitioners because of adverse effects or ineffectiveness of the antimicrobial agent(s).

In some embodiments, the composition further comprises an antimicrobial agent as an immediate release agent wherein the immediate release antimicrobial agent is the same agent as the controlled-release agent, a different antimicrobial agent, an additional therapeutic agent, or a combination thereof. In some embodiments, the composition further comprises an additional therapeutic agent, including an additional antimicrobial agent, an anti-inflammatory agent, a corticosteroid, a cytotoxic agent, an anti-TNF agent, a collagen, a gamma-globulin, an interferon, a platelet activator factor antagonist, a nitric oxide synthase inhibitor, or combinations thereof. In another aspect, the additional therapeutic agent is an immediate release or a controlled release agent.

In some embodiments, the additional therapeutic agent is an immediate release agent. In some embodiments, the additional therapeutic agent is a controlled release agent.

Accordingly, provided herein are controlled release antimicrobial agent formulations and compositions to locally treat auris externa structures of subjects, thereby avoiding side effects as a result of systemic administration of the antimicrobial agents. The locally applied antimicrobial agent formulations and compositions are compatible with auris externa, and are administered either directly to the desired auris externa structure of a subject, e.g. the ear canal, or administered to a structure in direct communication with areas of the auris externa. By specifically targeting the auris externa of the subject, adverse side effects as a result of systemic treatment are avoided. Moreover, by providing a controlled release antimicrobial agent formulation or composition to treat otic disorders, a constant and/or extended source of antimicrobial agent is provided to the subject suffering from an otic disorder, reducing or eliminating the variability of treatment.

There is little guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of ear disease are often unreliable as a tool for testing therapeutics that are being developed for clinical approval.

Provided herein are otic formulations that feature suitable levels of pH, osmolarity, ionic balance, sterility, endotoxin and/or pyrogen levels. The auris compositions described herein are compatible with the microenvironment of the outer ear (e.g., the EAC) and are suitable for administration to humans. In some embodiments, the formulations described herein aid visualization of the administered compositions obviating the need for invasive procedures (e.g., removal of perilymph).

Provided herein are controlled release antimicrobial agent formulations and compositions to locally treat targeted auris structures of subjects, thereby avoiding side effects as a result of systemic administration of the antimicrobial agent formulations and compositions. The locally applied antimicrobial agent formulations and compositions and devices are compatible with the targeted auris structures, and administered either directly to the desired targeted auris structure, or administered to a structure in direct communication with areas of the auris externa. By specifically targeting an auris structure, adverse side effects as a result of systemic treatment are avoided. Thus, by providing a controlled release antimicrobial agent formulation or composition to treat otic disorders, a sustained, and/or extended source of antimicrobial agent is provided to the individual or patient suffering from an otic disorder, reducing or eliminating variability in treatment. Accordingly, one embodiment disclosed herein is to provide a composition that enables at least one antimicrobial agent to be released in therapeutically effective doses either at variable or constant rates such as to ensure a sustained release of the at least one agent.

In addition, the auris-acceptable sustained-release antimicrobial agent formulations and treatments described herein are provided to the target ear region of the individual in need, including the middle ear, and the individual in need is additionally administered an oral dose of antimicrobial agent. In some embodiments, the oral dose of antimicrobial agent is administered prior to administration of the auris-acceptable sustained-release antimicrobial agent formulation, and then the oral dose is tapered off over the period of time that the auris-acceptable sustained-release antimicrobial agent formulation is provided. Alternatively, the oral dose of antimicrobial agent is administered during administration of the auris-acceptable controlled-release antimicrobial agent formulation, and then the oral dose is tapered off over the period of time that the auris-acceptable controlled-release antimicrobial agent formulation is provided. Alternatively, the oral dose of antimicrobial agent is administered after administration of the auris-acceptable controlled-release antimicrobial agent formulation has been initiated, and then the oral dose is tapered off over the period of time that the auris-acceptable controlled-release antimicrobial agent formulation is provided.

In addition, the antimicrobial agent pharmaceutical compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated for the compositions and devices described herein are carriers, adjuvants and excipients that lack ototoxicity or are minimally ototoxic in order to allow effective treatment of the otic disorders contemplated herein with minimal side effects in the targeted regions or areas.

By way of non-limiting example, the formulations disclosed herein may be free or substantially free of alcohols, propylene glycol, and cyclohexane. In some embodiments, the formulations disclosed herein comprise less than about 50 ppm, less than about 25 ppm, less than about 20 ppm, less than about 10 ppm, less than about 5 ppm, less than about 1 ppm, of each of alcohols, propylene glycol, and cyclohexane.

In some embodiment, the use of preservatives is limited, reduced or eliminated when formulating the auris-acceptable sustained release formulation disclosed herein. As a non-limiting example, the use of the following commonly utilized preservatives may be limited, reduced or eliminated when formulating agents for administration to the ear: benzethonium chloride, benzalkonium chloride, butylated hydroxytoluene (BHT), and thiomersal. Thus, in some embodiments, the formulations disclosed herein are free or substantially free of benzethonium chloride, benzalkonium chloride, butylated hydroxytoluene (BHT), and thiomersal. In some embodiments, the formulations disclosed herein comprise less than about 50 ppm, less than about 25 ppm, less than about 20 ppm, less than about 10 ppm, less than about 5 ppm, less than about 1 ppm, of each of benzethonium chloride, benzalkonium chloride, butylated hydroxytoluene (BHT), and thiomersal.

Certain antiseptics used to disinfect components of therapeutic preparations (or the devices utilized to administer the preparations) should be limited, reduced, or eliminated in otic preparations. For example, acetic acid, iodine, and merbromin are all known to be ototoxic. Additionally, chlorhexidene, a commonly used antiseptic, should be limited, reduced or eliminated to disinfect any component of an otic preparation (including devices used to administer the preparation) as it is highly ototoxic in minute concentrations (e.g., 0.05%). Thus, in some embodiments, the formulations disclosed herein are free or substantially free of acetic acid, iodine, merbromin, and chlorhexidene. In some embodiments, the formulations disclosed herein comprise less than about 50 ppm, less than about 25 ppm, less than about 20 ppm, less than about 10 ppm, less than about 5 ppm, less than about 1 ppm, of each of acetic acid, iodine, merbromin, and chlorhexidene.

Further, otic preparations require particularly low concentrations of several potentially-common contaminants that are known to be ototoxic. Other dosage forms, while seeking to limit the contamination attributable to these compounds, do not require the stringent precautions that otic preparations require. For example, the following contaminants should be absent or nearly absent from otic preparations: arsenic, lead, mercury, and tin. Thus, in some embodiments, a device disclosed herein is free or substantially free of arsenic, lead, mercury, and tin. In some embodiments, a device disclosed herein comprises less than about 50 ppm, less than about 25 ppm, less than about 20 ppm, less than about 10 ppm, less than about 5 ppm, less than about 1 ppm, of each of arsenic, lead, mercury, and tin.

Certain Definitions

The term "auris-acceptable" with respect to a formulation, composition or ingredient, as used herein, includes having no persistent detrimental effect on the auris externa (or external ear) of the subject being treated. By "auris-pharmaceutically acceptable," as used herein, refers to a material, such as a carrier or diluent, which does not abrogate the biological activity or properties of the compound in reference to the auris externa (or external ear), and is relatively or is reduced in toxicity to the auris externa (or external ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

The term "about" refers to a variation customarily understood in the technical field of the present disclosure. In some embodiment, the term "about" refers to a variation of ±20%. In some embodiments, the term "about" refers to a variation of ±15%. In some embodiments, the term "about" refers to a variation of ±10%. In some embodiments, the term "about" refers to a variation of ±5%. In some embodiments, the term "about" refers to a variation of ±2%. In some embodiments, the term "about" refers to a variation of ±1%.

"Auris externa" refers to the external ear, including the auditory canal, also referred to as the ear canal.

"Blood plasma concentration" refers to the concentration of compounds provided herein in the plasma component of blood of a subject.

The term "diluent" refers to chemical compounds that are used to dilute the antimicrobial agent prior to delivery and which are compatible with the auris externa.

The terms "co-administration" or the like, as used herein, are meant to encompass administration of the antimicrobial agents to a single patient, and are intended to include treatment regimens in which the antimicrobial agents are administered by the same or different route of administration or at the same or different time.

The terms "effective amount" or "therapeutically effective amount," as used herein, refer to a sufficient amount of the active agent or otic agent (e.g., an antimicrobial agent, an anti-inflammatory agent) being administered that would be expected to relieve to some extent one or more of the symptoms of the disease or condition being treated. For example, the result of administration of an antimicrobial agent disclosed herein is reduction and/or alleviation of the signs, symptoms, or causes of tinnitus or balance disorders. For example, an "effective amount" for therapeutic uses is the amount of antimicrobial agent, including a formulation as disclosed herein required to provide a decrease or amelioration in disease symptoms without undue adverse side effects. The term "therapeutically effective amount" includes, for example, a prophylactically effective amount. An "effective amount" of an antimicrobial agent disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

The terms "enhance" or "enhancing" refers to an increase or prolongation of either the potency or duration of a desired effect of antimicrobial agent, or a diminution of any adverse symptomatology that is consequent upon the administration of the therapeutic agent. Thus, in regard to enhancing the effect of the antimicrobial agents disclosed herein, the term "enhancing" refers to the ability to increase or prolong, either in potency or duration, the effect of other therapeutic agents that are used in combination with the antimicrobial agent disclosed herein. An "enhancing-effective amount," as used herein, refers to an amount of antimicrobial agent or other therapeutic agent which is adequate to enhance the effect of another therapeutic agent or antimicrobial agent of the target auris structure in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, or advancement of a condition in a patient necessitating treatment.

The terms "kit" and "article of manufacture" are used as synonyms.

"Pharmacodynamics" refers to the factors which determine the biologic response observed relative to the concentration of drug at the desired site within the auris externa.

"Pharmacokinetics" refers to the factors which determine the attainment and maintenance of the appropriate concentration of drug at the desired site within the auris externa.

As used herein, the term "antimicrobial agent" refers to compounds that inhibit the growth, proliferation, or multiplication of microbes, or that kill microbes. "Antimicrobial agents" may work by any suitable mechanism against the microbes, including by being toxic or cytostatic.

The term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, tympanostomy tubes, short electrodes, micro-prostheses or piston-like prostheses; needles; stem cell transplants; drug delivery devices; any cell-based therapeutic; or the like. Otic surgery includes middle ear surgery, inner ear surgery, tympanostomy, cochleostomy, labyrinthotomy, mastoidectomy, stapedectomy, stapedotomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

In prophylactic applications, compositions comprising the antimicrobial agents described herein are administered to a patient susceptible to or otherwise at risk of a particular disease, disorder or condition. For example, such conditions include and are not limited to otitis externa, otitis media, Ramsay Hunt syndrome, otosyphilis, AIED, Meniere's disease, and vestibular neuronitis. Such an amount is defined to be a "prophylactically effective amount or dose." In this use, the precise amounts also depend on the patient's state of health, weight, and the like.

As used herein "micronized ciprofloxacin" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent. In some embodiment, the "micronized ciprofloxacin" refers to micronized particles that are non-microencapsulated.

The mean residence time (MRT) is the average time that molecules of an active agent (e.g., a microbial agent) reside in an otic structure after a dose.

As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition, for example tinnitus, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Methods

Provided herein in some embodiments are methods of treating an otic disease or condition associated with a microbial infection. In some embodiments, the method comprises administering to a subject a composition comprising micronized ciprofloxacin and poloxamer 407.

In some embodiments, the otic disease or condition is associated with a bacterial infection. In certain embodiments, the otic disease or condition is associated with *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof. In some embodiments, the pediatric otic disease or condition is associated with *Streptococcus pneumoniae, Haemophilus influenzae, Moraxella catarrhalis, Streptococcus pyogenes, Staphylococcus aureus*, or a combination thereof. In some embodiments, the pediatric otic disease or condition is associated with *Streptococcus pneumonia*. In some embodiments, the pediatric otic disease or condition is associated with *Haemophilus influenzae*. In some embodiments, the otic disease or condition is associated with *Moraxella catarrhalis*.

In some embodiments, the compositions described herein treat an otic disease or condition associated with traditionally resistant bacterial strains. In some embodiments, the compositions described herein treat an otic disease or condition associated with intermediate and resistant bacterial strains to ciprofloxacin. In some embodiments, the intermediate and resistant bacterial strains to ciprofloxacin exhibit a MIC above 2 μg/mL, above 25 μg/mL, above 50 μg/mL, or above 75 μg/mL.

In some embodiments, use of the compositions described herein provide adequate clinical cure against resistant microorganisms. In some embodiments, the time to clinical cure is 6 h, 8 h, 10 h, 12 h, 14 h, 16 h, 18 h, 20 h, 22 h, 24 h, 26 h, 28 h, 30 h, 32 h, 34 h, 36 h, 38 h, 40 h, 42 h, 44 h, 48 h, 50 h, 52 h, 54 h, 56 h, 58 h, 60 h, 64 h, 68 h, or 72 h. In certain embodiments, the time to clinical cure is about 12 h. In some embodiments, the time to clinical cure is less than 12 h. In certain embodiments, the time to clinical cure is about 18 h. In some embodiments, the time to clinical cure is less than 18 h. In certain embodiments, the time to clinical cure is about 24 h. In some embodiments, the time to clinical cure is less than 24 h. In certain embodiments, the time to clinical cure is about 36 h. In some embodiments, the time to clinical cure is less than 36 h. In certain embodiments, the time to clinical cure is about 48 h. In some embodiments, the time to clinical cure is less than 48 h. In certain embodiments, the resistant microorganisms are resistant to ciprofloxacin. In some embodiments, the methods described herein prevent or alleviate the potential for antibiotic resistance. In some embodiments, the use of the compositions described herein provides bacterial eradication. In certain embodiments, the methods described herein eradicate pre-therapy bacteria in the middle ear. In some embodiments, the use of the compositions described herein reduces middle ear effusion.

In some embodiments, the use of the compositions provided herein provides antimicrobial protection against biofilms. In some embodiments, the biofilms are present on tympanostomy tubes placed in a subject. In some embodiments, the compositions provided herein disrupt biofilms.

Some embodiments provided herein describe a method of treating or preventing post-surgical otorrhea. In some embodiments, the method comprises administering to a subject a composition comprising micronized ciprofloxacin and poloxamer 407. In some embodiments, there is no visible otorrhea 3 days post-surgery. In other embodiments, there is no visible otorrhea 5 days post-surgery. In other embodiments, there is no visible otorrhea 7 days post-surgery. In other embodiments, there is no visible otorrhea 10 days post-surgery. In other embodiments, there is no visible otorrhea 14 days post-surgery.

In some embodiments, the methods described herein treat otic diseases or conditions without causing or leading to ototoxicity. In some embodiments, treatment of an otic disease or condition with a composition described herein provides minimal functional changes in hearing. In some embodiments, treatment of an otic disease or condition with a composition described herein provides no evidence of cochlear pathology. In some embodiments, treatment of an otic disease or condition with a composition described herein provides minimal threshold shifts. In some embodiments, treatment of an otic disease or condition with a composition described herein does not change or influence cochlear pathology. In some embodiments, treatment of an otic disease or condition with a composition described herein is not associated with cochlear toxicity. In some embodiments, treatment of an otic disease or condition with a composition described herein does not induce hair cell loss of the cochlea. In some embodiments, treatment of an otic disease or condition with a composition described herein does not affect the patency of tympanostomy tubes.
eb;normal Anatomy of the Ear As shown in FIG. 1, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Diseases & Conditions

Otic disorders, including auris interna, auris media, and auris externa disorders, produce symptoms which include but are not limited to hearing loss, nystagmus, vertigo, tinnitus, inflammation, swelling, infection and congestion. These disorders may have many causes, such as infection, injury, inflammation, tumors and adverse response to drugs or other chemical agents. While the formulations disclosed herein are particularly suited for diseases and conditions affecting the outer ear/EAC, it is also contemplated that administration of these formulations to the outer ear may also be useful, perhaps in combination with other therapeutic agents or therapeutic methods, to treat any otic disorder or combination of otic disorders, or consequences of an otic disorder. Thus, a non-exhaustive description of otic disorders are described herein.

Inflammatory Disorders of the Ear

Otitis externa (OE), also referred to as swimmer's ear, is an inflammation and/or infection of the external ear. OE is often caused by bacteria in the outer ear, which establish infection following damage to the skin of the ear canal. Primary bacterial pathogens that cause OE are *Pseudomonas aeruginosa* and *Staphylococcus aureus*, but the condition is associated with the presence of many other strains of gram positive and negative bacteria. OE is also sometimes caused by fungal infection in the outer ear, including *Candida albicans* and *Aspergillus*. Symptoms of OE include otalgia, swelling, and otorrhea. If the condition progresses significantly, OE may cause temporary conductive hearing loss as a result of the swelling and discharge.

Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids. Typical antibacterial agents for the treatment of OE include aminoglycosides (e.g., neomycin, gentamycin, and tobramycin), polymyxins (e.g., polymyxin B), fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, cefibuten, and ceftriaxone), penicillins (e.g., amoxicillin, amoxicillin-clavulanate, and penicillinase-resistant penicillins), and combinations thereof. Typical antifungal agents for the treatment of OE include clotrimazole, thimerasol, M-cresyl acetate, tolnaftate, itraconazole, and combinations thereof. Acetic acid is also administered to the ear, alone and in combination with other agents, to treat bacterial and fungal infections. Ear drops are often used as the vehicle for administration of the active agents. In the case that ear swelling has progressed substantially and ear drops do not penetrate significantly into the ear canal, a wick can be inserted into the ear canal to facilitate penetration of the treatment solutions. Oral antibiotics are also administered in the case of extensive soft tissue swelling that extends to the face and neck. When the pain of OE is extremely severe such that it interferes with normal activity, e.g., sleeping, pain relievers such as topical analgesics or oral narcotics may be given until the underlying inflammation and infection are alleviated.

Notably, some types of topical ear drops, such as ear drops containing neomycin, are safe and effective for use in the ear canal, but can be irritating and even ototoxic to the auris media, prompting concern that such topical preparations should not be used unless the tympanic membrane is known to be intact. Utilization of the formulations disclosed herein for the treatment of OE allows for use of active agents that are potentially damaging to the auris media, even when the tympanic membrane is not intact. Specifically, the controlled release formulations disclosed herein can be applied locally in the external ear with improved retention time, thus eliminating concern that the active agents will leak out of the ear canal into the auris media. Furthermore, otoprotectants can be added when ototoxic agents, such as neomycin, are used.

Treatment of severe OE with the antimicrobial compositions disclosed herein, particularly highly viscous and/or mucoadhesive formulations, also obviates the need for extended use of an ear wick. Specifically, the compositions disclosed herein have increased retention time in the ear canal as a result of the formulation technology, thus eliminating the need for a device to maintain their presence in the outer ear. The formulations can be applied in the outer ear with a needle or an ear dropper, and the active agents can be maintained at the site of inflammation without the aid of an ear wick. In some embodiments, antimicrobial agent compositions described herein further comprise anti-inflammatory agents and are useful in the treatment of otitis externa.

In some embodiments, the treatment of OE with antimicrobial formulations disclosed herein encompasses the treatment of granular myringitis, a specific form of OE characterized by chronic inflammation of the pars tensa of the tympanic membrane. The outer epithelial and underlying fibrous layers of the tympanic membrane are replaced by a proliferating granulation tissue. The predominant symptom is foul-smelling otorrhea. A variety of bacteria and fungi cause the condition, including *Proteus* and *Psuedomonas* species. Accordingly, antimicrobial agent formulations disclosed herein comprising antibacterial or antifungal agents are useful for the treatment of granular myringitis.

In some embodiments, the treatment of OE with antimicrobial formulations disclosed herein encompasses the treatment of chronic stenosing otitis externa. Chronic stenosing otitis externa is characterized by repeated infections, typically caused by bacteria or fungi. The primary symptoms are pruritus in the ear canal, otorrhea, and chronic swelling. Antimicrobial agent formulations disclosed herein comprising antibacterial or antifungal agents are useful for the treatment of chronic stenosing otitis externa.

In some embodiments, the treatment of OE with antimicrobial formulations disclosed herein encompasses the treatment of malignant or necrotizing external otitis, an infection involving the temporal and adjacent bones. Malignant external otitis is typically a complication of external otitis. It occurs primarily in persons with compromised immunity, especially in older persons with diabetes mellitus. Malignant external otitis is often caused by the bacteria *Pseudomonas aeruginosa*. Treatment typically involves correction of immunosuppression when possible, in conjunction with antibacterial therapy and pain relievers. According, antimicrobial agent formulations disclosed herein are useful for the treatment of malignant or necrotizing external otitis.

In some embodiments, antimicrobial formulations disclosed herein are also useful for the treatment of temporal bone osteoradionecrosis.

Acute Otitis Externa (AOE)

AOE is a condition of the ear characterized by inflammation of the ear canal. Symptoms of AOE include, but are not limited to, swelling of the ear canal, decreased hearing, ear discharge, itchiness, skin shedding of the ear canal, redness of the ear canal, lack of cerumen, and pain of the outer ear. AOE may be diagnosed by pushing or pulling an outer ear structure, such as the auricle, and determining if any pain is associated with this activity. OE may be characterized as acute when the subject has experienced these symptoms for less than six weeks, less than eight weeks or less than 12 weeks. AOE is typically accompanied or caused by a bacterial infection of the ear or surrounding skin. AOE may also be accompanied by a fungal infection. In some embodiments, the AOE is caused by or promoted by use of a hearing aid, use of an ear plug, swimming, psoriasis, atopic dermatitis, seborrheic dermatitis, or diabetes.

AOE is a common condition in the pediatric population characterized by diffuse inflammation of the external acoustic meatus. The 2001 to 2007 data from the Centers for Disease Control and Prevention estimate a yearly incidence of 8.1 per 1000 population, with a higher incidence during the summer months in children between the ages of 5 and 14 years old, but is also widely known to occur in adults. A diagnosis of AOE requires a rapid onset (within 48 hours) of signs and symptoms of external acoustic meatus inflammation with or without infection. Typical symptoms include otalgia, itching, and aural fullness. Signs include tenderness of the tragus and pinna, diffuse ear canal edema, conductive hearing loss, erythema, and otorrhea. Overall 90% of AOE cases are unilateral, and in North America more than 90% of the time AOE is caused by bacterial infection, with a low incidence of fungal infection. *Pseudomonas aeruginosa* and *Staphylococcus aureus* are the most common pathogens responsible for AOE, with *Staphylococcus* species being less prevalent in children than in adults.

Ear Pruritus

Ear pruritus, or itchy ear canal, is a tickling or irritating sensation that causes a desire or reflex to scratch the affected area. In some cases, redness, swelling, soreness and flaking may develop in the affected area. Ear pruritus is caused by a variety of agents. In some embodiments, ear pruritus occurs due to either primary microbial infection within the ear or as a secondary infection from the body where it is then spread into the ear canal. In some embodiments, skin conditions such as eczema or psoriasis lead to skin irritations within the ear canal. Further, external irritants such as hairspray, shampoo, shower gel, or allergen such as dust, pets, and pollen, can lead to ear pruritus. In some embodiments, ear pruritus serves as an early sign for more serious complications such as otitis externa.

Otalgia

Otalgia, also known as earache or ear pain, is classified into two types, primary otalgia and referred otalgia. Primary otalgia is ear pain which originates from inside of the ear. Referred otalgia is ear pain which originates from the outside of the ear. Although the etiology of referred otalgia can be complex, several well-known culprits include dental disorders, sinusitis, neck problems, tonsillitis, pharyngitis, and sensory branches from the vagus and glossopharyngeal nerves. In some cases, referred otalgia has been associated with head and neck malignancies.

Ear Fullness

Ear fullness or aural fullness is described as a feeling that the ears are clogged, stuffed, or congested. Similar to otalgia, the etiology of ear fullness is diverse with numerous underlying causes. Generally, ear fullness may also be accompanied by tinnitus, otalgia, and impaired hearing.

Pharmaceutical Agents

Provided herein are antimicrobial agent compositions and formulations that treat otic disorders and/or their attendant symptoms, including but not limited to infection, hearing loss, nystagmus, vertigo, tinnitus, inflammation, swelling, and congestion. Otic disorders, including AIED, otitis media, otitis externa, Meniere's disease, Ramsay Hunt syndrome, otosyphilis, hereditary disorders and vestibular neuronitis, have causes and symptoms that are responsive to the pharmaceutical agents disclosed herein, or other pharmaceutical agents. Antimicrobial agents that are not disclosed herein but which are useful for the amelioration or eradication of otic disorders are expressly included and intended within the scope of the embodiments presented. In some embodiments, pharmaceutically active metabolites, salts, polymorphs, prodrugs, analogues, and derivatives of the antimicrobial agents disclosed herein that retain the ability of the parent antimicrobial agents to treat otic disorders are useful in the formulations.

Moreover, pharmaceutical agents which have been previously shown to be excessively toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways, or through poor PK characteristics, are useful in some embodiments. Accordingly, pharmaceutical agents which have limited or no systemic release, systemic toxicity, poor PK characteristics or combinations thereof are contemplated within the scope of the embodiments disclosed herein.

Antimicrobial Agent

Some embodiments provided herein describe composition comprising an antimicrobial agent. In some embodiments, the antimicrobial agent is an antibacterial agent. In some embodiments, the antibacterial agent treats infections caused by gram positive bacteria. In some embodiments, the antibacterial agent treats infections caused by gram negative bacteria. In some embodiments, the antibacterial agent treats infections caused by mycobacteria. In some embodiments, the antibacterial agent treats infections caused by giardia. In some embodiments, the antibacterial agent (e.g., ciprofloxacin) treats infections caused by *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof. In some embodiments, the antibacterial agent (e.g., ciprofloxacin) treats infections caused by *Streptococcus pneumoniae, Haemophilus influenzae, Moraxella catarrhalis, Streptococcus pyogenes, Staphylococcus aureus*, or a combination thereof. In some embodiments, the antibacterial agent (e.g., ciprofloxacin) treats infections caused by *Streptococcus pneumonia*. In some embodiments, the antibacterial agent (e.g., ciprofloxacin) treats infections caused by *Haemophilus influenzae*. In some embodiments, the antibacterial agent (e.g., ciprofloxacin) treats infections caused by *Moraxella catarrhalis*.

In some embodiments, the antibacterial agent treats infections by inhibiting bacterial protein synthesis. In some embodiments, the antibacterial agent treats infections by disrupting synthesis of bacterial cell wall. In some embodiments, the antibacterial agent treats infections by changing permeability of bacterial cell membranes. In some embodiments, the antibacterial agent treats infections by disrupting DNA replication in bacteria.

In some embodiments, the antibacterial agent is an antibiotic. In some embodiments, the antibiotic is a quinolone. In specific embodiments, the antibiotic is ciprofloxacin. In some embodiments, the antibiotic is micronized ciprofloxacin. In some embodiments, an antibiotic compatible with the compositions described herein is a broad spectrum antibiotic. In some embodiments, an antibiotic compatible with the compositions described herein is effective in treating infections that are resistant to other classes of antibiotics. In some embodiments, intratympanic administration of an antibiotic composition described herein reduces the risk of development of antibiotic resistance that is seen with systemic treatments.

Concentration of Active Agent

In some embodiments, the compositions described herein have a concentration of active pharmaceutical ingredient between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the active ingredient, or pharmaceutically acceptable prodrug or salt thereof, by weight of the composition. In some embodiments, the compositions described herein have a concentration of active pharmaceutical agent, or pharmaceutically acceptable prodrug or salt thereof, between about 1% to about 50%, between about 5% to about 50%, between about 10% to about 40%, or between about 10% to about 30%, of the active ingredient, or pharmaceutically acceptable prodrug or salt thereof, by weight of the composition. In some embodiments, formulations described herein comprise about 70% by weight of an antimicrobial agent, or pharmaceutically acceptable prodrug or salt thereof, by weight of the formulation. In some embodiments, formulations described herein comprise about 60% by weight of an antimicrobial agent, or pharmaceutically acceptable prodrug or salt thereof, by weight of the formulation. In some embodiments, formulations described herein comprise about 50% by weight of an antimicrobial agent, or pharmaceutically acceptable prodrug or salt thereof, by weight of the formulation. In some embodiments, formulations described herein comprise about 40% by weight of an antimicrobial agent, or pharmaceutically acceptable prodrug or salt thereof, by weight of the formulation. In some embodiments, formulations described herein comprise about 30% by weight, or pharmaceutically acceptable prodrug or salt thereof, of an antimicrobial agent by weight of the formulation. In some embodiments, formulations described herein comprise about 20% by weight of an antimicrobial agent, or pharmaceutically acceptable prodrug or salt thereof, by weight of the formulation. In some embodiments, formulations described herein comprise about 15% by weight of an antimicrobial agent, or pharmaceutically acceptable prodrug or salt thereof, by weight of the formulation. In some embodiments, formulations described herein comprise about 10% by weight of an antimicrobial agent by weight of the formulation. In some embodiments, formulations described herein comprise about 5% by weight of an antimicrobial agent, or pharmaceutically acceptable prodrug or salt thereof, by weight of the formulation. In some embodiments, formulations described herein comprise about 2.5% by weight of an antimicrobial agent, or pharmaceutically acceptable prodrug or salt thereof, by weight of the formulation. In some embodiments, formulations described herein comprise about 1% by weight of an antimicrobial agent, or pharmaceutically acceptable prodrug or salt thereof, by weight of the formulation. In some embodiments, formulations described herein comprise about 0.5% by weight of an antimicrobial agent, or pharmaceutically acceptable prodrug or salt thereof, by weight of the formulation. In some embodiments, formulations described herein comprise about 0.1% by weight of an antimicrobial agent, or pharmaceutically acceptable prodrug or salt thereof, by weight of the formulation. In some embodiments, formulations described herein comprise about 0.01% by weight of an antimicrobial agent, or pharmaceutically acceptable prodrug or salt thereof, by weight of the formulation.

In some embodiments, the formulations described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the formulation. In some embodiments, the formulations described herein have a concentration of active pharmaceutical ingredient, or pharmaceutically acceptable prodrug or salt thereof, between about 40 mg/mL to about 80 mg/mL. In some embodiments, the formulations described herein have a concentration of active pharmaceutical ingredient, or pharmaceutically acceptable prodrug or salt thereof, between about 50 mg/mL to about 70 mg/mL. In some embodiments, the formulations described herein have a concentration of active pharmaceutical ingredient, or pharmaceutically acceptable prodrug or salt thereof, between about 55 mg/mL to about 65 mg/mL. In some embodiments, the formulations described herein have a concentration of active pharmaceutical ingredient, or pharmaceutically acceptable prodrug or salt thereof, of about 40 mg/mL, about 45 mg/mL, about 50 mg/mL, about 55 mg/mL, about 60 mg/mL, about 65 mg/mL, about 70 mg/mL, about 75 mg/ml or about 80 mg/mL. to about 80 mg/mL. In some embodiments, the formulations described herein have a concentration of active pharmaceutical ingredient, or pharmaceutically acceptable prodrug or salt thereof, of about 60 mg/mL. In some embodiments, the formulations described herein have a concentration of active pharmaceutical ingredient, or pharmaceutically acceptable prodrug or salt thereof, of 60 mg/mL.

In some embodiments, the composition comprises 1-8% by weight of micronized ciprofloxacin. In some embodiments, the composition comprises 1.8 to 6.6% by weight of micronized ciprofloxacin. In some embodiments, the composition comprises 1.8-2.2% by weight of micronized ciprofloxacin. In other embodiments, the composition comprises 5.4-6.6% by weight of micronized ciprofloxacin. In some embodiments, the composition comprises about 1%, about 1.1% about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0% by weight of micronized ciprofloxacin. In some specific embodiments, the composition comprises about 1.8% by weight of micronized ciprofloxacin. In some specific embodiments, the composition comprises about 1.9% by weight of micronized ciprofloxacin. In some specific embodiments, the composition comprises about 2.0% by weight of micronized ciprofloxacin. In some specific embodiments, the composition comprises about 2.1% by weight of micronized ciprofloxacin. In some specific embodiments, the composition comprises 2.2% by weight of micronized ciprofloxacin. In some specific embodiments, the composition comprises 5.4% by weight of micronized ciprofloxacin. In some specific embodiments, the composition comprises 5.5% by weight of micronized ciprofloxacin. In some specific embodiments, the composition comprises 5.6% by weight of micronized ciprofloxacin. In some specific embodiments, the composition comprises 5.7% by weight of micronized ciprofloxacin. In some specific embodiments, the composition comprises 5.8% by weight of micronized ciprofloxacin. In some specific embodiments, the composition comprises 5.9% by weight of micronized ciprofloxacin. In some specific embodiments, the composition comprises 6.0% by weight of micronized ciprofloxacin. In some specific embodiments, the composition comprises 6.1% by weight of micronized ciprofloxacin. In some specific embodiments, the composition comprises 6.2% by weight of micronized ciprofloxacin. In some specific embodiments, the composition comprises 6.3% by weight of micronized ciprofloxacin. In some specific embodiments, the composition comprises 6.4% by weight of micronized ciprofloxacin. In some specific embodiments, the composition comprises 6.5% by weight of micronized ciprofloxacin. In some specific embodiments, the composition comprises 6.6% by weight of micronized ciprofloxacin.

In some embodiments, the formulations described herein have a concentration of ciprofloxacin between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL. In some embodiments, the formulations described herein have a concentration ciprofloxacin between about 40 mg/mL to about 80 mg/mL. In some embodiments, the formulations described herein have a concentration of ciprofloxacin between about 50 mg/mL to about 70 mg/mL. In some embodiments, the formulations described herein have a concentration of ciprofloxacin between about 55 mg/mL to about 65 mg/mL. In some embodiments, the formulations described herein have a concentration of ciprofloxacin of about 40 mg/mL, about 45 mg/mL, about 50 mg/mL, about 55 mg/mL, about 60 mg/mL, about 65 mg/mL, about 70 mg/mL, about 75 mg/ml or about 80 mg/mL to about 80 mg/mL. In some embodiments, the formulations described herein have a concentration of ciprofloxacin of about 60 mg/mL. In some embodiments, the formulations described herein have a concentration of ciprofloxacin of 60 mg/mL.

Pharmaceutical Formulations

Provided herein are pharmaceutical compositions or devices that include at least one antimicrobial agent (e.g., ciprofloxacin) and a pharmaceutically acceptable diluent(s), excipient(s), or carrier(s). In some embodiments, the pharmaceutical compositions include other medicinal or pharmaceutical agents, carriers, adjuvants, such as salts for regulating the osmotic pressure, and/or buffers. In other embodiments, the pharmaceutical compositions also contain other therapeutic substances. In some embodiments, the pharmaceutical compositions are preservative-free.

Figure 3:
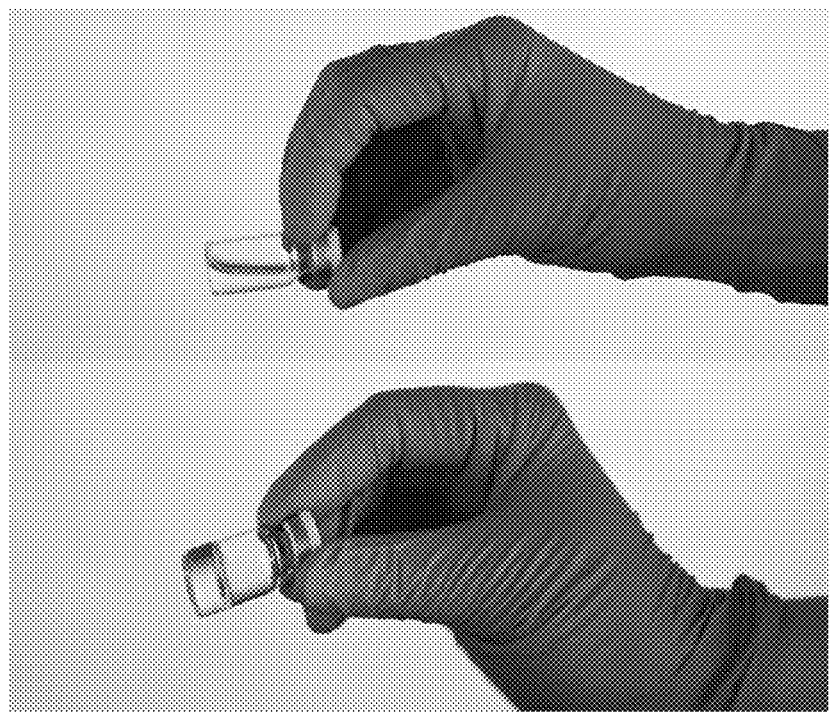
FIG. 3 depicts two physical states of the thermoreversible formulations disclosed herein: (1) a liquid, as the formulation will be before and as its administered, and (2) a solid, as the formulation will be after contact with the outer ear/ear canal.

In some embodiments, the otic pharmaceutical formulations described herein further provide an auris-acceptable hydrogel; in still further embodiments, the auris pharmaceutical formulations provide an auris-acceptable in situ forming hydrogel material. In some embodiments, the auris pharmaceutical formulations provide an auris-acceptable solvent release gel. In some embodiments, the auris pharmaceutical formulations provide an actinic radiation curable gel. Further embodiments include a thermoreversible gel in the auris pharmaceutical formulation, such that upon preparation of the gel at room temperature or below, the formulation is a fluid, but upon application of the gel into or near the EAC target site, including the outer surface of the tympanic membrane, the auris-pharmaceutical formulation stiffens or hardens into a gel-like substance (see, e.g., FIG. 3).

In some embodiments, the auris-compatible formulations described herein are free of preservatives. In some embodiments, any of the formulations described herein are free of sodium bisulfite, sodium thiosulfate, ascorbate, chorobutanol, thimerosal, parabens, benzyl alcohol, Butylated hydroxytoluene (BHT), and phenylethanol. In certain embodiments, any of the formulations described herein are free of BHT.

In some embodiments, the compositions described herein include a dye to help enhance the visualization of the gel when applied to the EAC. In some embodiments, dyes that are compatible with the auris-acceptable compositions described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g, FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MRI dyes, iodine-base dyes, barium-based dyes or the like are also contemplated for use with any otic formulation described herein. Other dyes that are compatible with any formulation or composition described herein are listed in the Sigma-Aldrich catalog under dyes (which is included herein by reference for such disclosure).

pH and Practical Osmolarity

In some embodiments, an otic composition or device disclosed herein is formulated to provide an ionic balance that is compatible with outer ear fluids or substances.

In certain instances, the ionic composition of the EAC regulates the electrochemical impulses of hair cells and thus hearing. In certain instances, changes in the conduction of electrochemical impulses along otic hair cells results in hearing loss. In certain instances, changes in the ionic balance of the EAC results in complete hearing loss. In certain instances, changes in the ionic balance of the EAC results in partial hearing loss. In certain instances, changes in the ionic balance of the EAC results in permanent hearing loss. In certain instances, changes in the ionic balance of the EAC results in temporary hearing loss.

In some embodiments, a composition or device disclosed herein is formulated in order to not disrupt the ionic balance of the endolymph. In some embodiments, a composition or device disclosed herein has an ionic balance that is the same as or substantially the same as the endolymph. In some embodiments, a composition or device disclosed herein does not does not disrupt the ionic balance of the endolymph so as to result in partial or complete hearing loss. In some embodiments, a composition or device disclosed herein does not does not disrupt the ionic balance of the endolymph so as to result in temporary or permanent hearing loss.

In some embodiments, a composition or device disclosed herein does not substantially disrupt the ionic balance of the EAC. In some embodiments, a composition or device disclosed herein has an ionic balance that is the same as or substantially the same as the EAC. In some embodiments, a composition or device disclosed herein does not result in partial or complete hearing loss as the composition or device does not disrupt the ionic balance of the EAC. In some embodiments, a composition or device disclosed herein does not result in temporary or permanent hearing loss as the composition or device does not disrupt the ionic balance of the EAC.

As used herein, "practical osmolarity/osmolality" or "deliverable osmolarity/osmolality" means the osmolarity/osmolality of a composition or device as determined by measuring the osmolarity/osmolality of the active agent and all excipients except the gelling and/or the thickening agent (e.g., polyoxyethylene-polyooxypropylene copolymers, carboxymethylcellulose or the like). The practical osmolarity of a composition or device disclosed herein is measured by a suitable method, e.g., a freezing point depression method as described in Viegas et. al., *Int. J. Pharm.*, 1998, 160, 157-162. In some instances, the practical osmolarity of a composition or device disclosed herein is measured by vapor pressure osmometry (e.g., vapor pressure depression method) that allows for determination of the osmolarity of a composition or device at higher temperatures. In some instances, vapor pressure depression method allows for determination of the osmolarity of a composition or device comprising a gelling agent (e.g., a thermoreversible polymer) at a higher temperature wherein the gelling agent is in the form of a gel.

In some embodiments, the osmolarity at a target site of action (e.g., the EAC) is about the same as the delivered osmolarity (i.e., osmolarity of materials that cross or penetrate the round window membrane) of a composition or device described herein. In some embodiments, a composition or device described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an otic composition or device disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition or device described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

Some embodiments provided herein describe an antimicrobial composition further comprising an osmolality modifier, pH adjusting agent, and a buffering agent. In some embodiments, the antimicrobial composition comprises hydrochloric acid as a pH adjusting agent. In some embodiments, the antimicrobial composition comprises tromethamine as a buffering agent. In some embodiments, the antimicrobial composition comprises sodium chloride as an osmolality modifier. In certain embodiments, the antimicrobial composition consists of ciprofloxacin, poloxamer 407, water, an osmolality modifier (e.g., sodium chloride), a pH adjusting agent (e.g., hydrochloric acid), and a buffering agent (e.g., tromethamine).

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g, by filtration or aseptic mixing or heat treatment and/or autoclaving (e.g., terminal sterilization)) of a gel formulation without degradation of the pharmaceutical agent (e.g., antimicrobial agent) or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for sterilization (e.g, by heat treatment and/or autoclaving) of a gel formulation without degradation of the pharmaceutical agent (e.g., antimicrobial agent) or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g, by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g, by filtration or aseptic mixing or heat treatment and/or autoclaving (e.g., terminal sterilization)) of any composition described herein.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In specific embodiments, the deliverable osmolarity/osmolality of the formulations (i.e., the osmolarity/osmolality of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations EAC-compatible (i.e. isotonic with the EAC) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., EAC) that causes minimal disturbance to the environment of the outer ear and causes minimum discomfort (e.g., vertigo and/or nausea) to a mammal upon administration.

In other embodiments, the gel formulation is isotonic with the EAC. Isotonic formulations are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/kg to about 400 mOsm/kg, from about 280 mOsm/kg to about 320 mOsm/kg. The amount of tonicity agents will depend on the target structure of the pharmaceutical formulation, as described herein.

Useful tonicity compositions also include one or more salts in an amount required to bring osmolality of the composition into an acceptable range for application to the EAC. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the formulations described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and/or practical osmolarity as described herein, and have a concentration of active pharmaceutical ingredient between about 0.01%-about 20%, between about 0.01%-about 10%, between about 0.01%-about 7.5%, between about 0.01%-6%, between about 0.01-5%, between about 0.1-about 10%, or between about 0.1-about 6% of the active ingredient by weight of the formulation. In some embodiments, the formulations described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation. In some embodiments, the formulations described herein have a pH and/or practical osmolarity as described herein, and have a concentration of active pharmaceutical ingredient between about 1 µg/mL and about 500 µg/mL, between about 1 µg/mL and about 250 µg/mL, between about 1 µg and about 100 µg/mL, between about 1 µg/mL and about 50 µg/mL, or between about 1 µg/mL and about 20 µg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e., the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 µm to about 100 µm. In some embodiments, the average diameter of particles in a micronized solid is from about 3 µm to about 50 µm. In some embodiments, a particulate micronized solid comprises particle sizes of less than about 5 microns, less than about 20 microns and/or less than about 100 microns. In some embodiments, the use of particulates (e.g., micronized particles) of antimicrobial agent allows for extended and/or sustained release of the antimicrobial agent from any formulation described herein compared to a formulation comprising non-multiparticulate (e.g, non-micronized) antimicrobial agent. In some instances, formulations containing multiparticulate (e.g. micronized) antimicrobial agent are ejected from a 1 mL syringe adapted with a 27 G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

In some embodiments, a formulation described herein comprises one or more antimicrobial agents wherein the antimicrobial agent comprises nanoparticulates. In some embodiments, a formulation described herein comprises antimicrobial agent beads (e.g., vancomycin beads) that are optionally coated with controlled release excipients. In some embodiments, a formulation described herein comprises an antimicrobial agent that is granulated and/or reduced in size and coated with controlled release excipients; the granulated coated antimicrobial agent particulates are then optionally micronized and/or formulated in any of the compositions described herein.

In some instances, a combination of an antimicrobial agent as a neutral molecule, free acid or free base and/or a salt of the antimicrobial agent is used to prepare pulsed release otic agent formulations using the procedures described herein. In some formulations, a combination of a micronized antimicrobial agent (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the antimicrobial agent (e.g., micronized antimicrobial agent, free base, free acid or salt or prodrug thereof; multiparticulate antimicrobial agent, free base, free acid or salt or prodrug thereof) with the aid of cyclodextrins, surfactants (e.g., poloxamers (407, 338, 188), tween (80, 60, 20,81), PEG-hydrogenated castor oil, cosolvents like N-methyl-2-Pyrrolidone or the like and preparing pulsed release formulations using any procedure described herein.

In specific embodiments, any auris-compatible formulation described herein comprises one or more micronized pharmaceutical agents (e.g., antimicrobial agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises an antimicrobial agent as a neutral molecule, a free acid, a free base, a salt, a prodrug or any combination thereof. In certain embodiments, a pharmaceutical composition described herein comprises an antimicrobial agent as a micronized powder. In certain embodiments, a pharmaceutical composition described herein comprises an antimicrobial agent in the form of a micronized antimicrobial agent powder.

The multiparticulates and/or micronized antimicrobial agents described herein are delivered to an auris structure (e.g., outer ear) by means of any type of matrix including solid, liquid or gel matrices. In some embodiments, the multiparticulates and/or micronized antimicrobial agents described herein are delivered to an auris structure (e.g., outer ear) by means of any type of matrix including solid, liquid or gel matrices via intratympanic injection.

Tunable Release Characteristics

The release of active agent from any formulation, composition or device described herein is optionally tunable to the desired release characteristics. In some embodiments, a composition described herein is a solution that is substantially free of gelling components. In such instances, the composition provides essentially immediate release of an active agent. In some of such embodiments, the composition is useful in perfusion of otic structures, e.g., during surgery.

In some embodiments, a composition described herein is a solution that is substantially free of gelling components and comprises micronized otic agent (e.g., a corticosteroid, an antimicrobial agent or the like). In some of such embodiments, the composition provides release of an active agent from about 2 days to about 4 days.

In some embodiments, a composition described herein comprises a gelling agent (e.g., poloxamer 407) and provides release of an active agent over a period of from about 1 day to about 3 days. In some embodiments, a composition described herein comprises a gelling agent (e.g., poloxamer 407) and provides release of an active agent over a period of from about 1 day to about 5 days. In some embodiments, a composition described herein comprises a gelling agent (e.g., poloxamer 407) and provides release of an active agent over a period of from about 2 days to about 7 days.

In some embodiments, a composition described herein comprises a thermoreversible polymer (e.g., poloxamer 407) in combination with micronized otic agent (e.g., ciprofloxacin) and provides extended sustained release over a longer period of time. In some embodiments, a composition described herein comprises about 14-17% of a thermoreversible polymer (e.g., poloxamer 407) and micronized otic agent (e.g., ciprofloxacin), and provides extended sustained release over a period of from about 1 week to about 3 weeks. In some embodiments, a composition described herein comprises about 18-21% of a thermoreversible polymer (e.g., poloxamer 407) and micronized otic agent (e.g., ciprofloxacin), and provides extended sustained release over a period of from about 3 weeks to about 6 weeks. In some embodiments, a composition described herein comprises about 15-17% by weight of a thermoreversible polymer (e.g., poloxamer 407). In some embodiments, a composition described herein comprises about 14.4-17.6% by weight of a thermoreversible polymer (e.g., poloxamer 407). In some embodiments, a composition described herein comprises about 15.5-16.5% by weight of a thermoreversible polymer (e.g., poloxamer 407). In some embodiments, a composition described herein comprises about 14.4%, about 14.6%, about 14.8%, about 15%, about 15.1%, about 15.2%, about 15.3%, about 15.4%, about 15.5%, about 15.6%, about 15.7%, about 15.8%, about 15.9%, about 16%, about 16.1%, about 16.2%, about 16.3%, about 16.4%, about 16.5%, about 16.6%, about 16.7%, about 16.8%, about 16.9%, about 17%, about 17.2%, about 17.4%, about 17.6%, about 17.8%, about 18% by weight of a thermoreversible polymer (e.g., poloxamer 407). In some embodiments, a composition described herein comprises about 15% by weight of a thermoreversible polymer (e.g., poloxamer 407). In some embodiments, a composition described herein comprises about 15.5% by weight of a thermoreversible polymer (e.g., poloxamer 407). In some embodiments, a composition described herein comprises about 16% by weight of a thermoreversible polymer (e.g., poloxamer 407). In some embodiments, a composition described herein comprises about 16.5% by weight of a thermoreversible polymer (e.g., poloxamer 407). In some embodiments, a composition described herein comprises about 17% by weight of a thermoreversible polymer (e.g., poloxamer 407).

Accordingly, the amount of gelling agent in a composition, and the particle size of an otic agent are tunable to the desired release profile of an otic agent from the composition.

As described herein, compositions comprising micronized otic agents (e.g., ciprofloxacin) provide extended release over a longer period of time compared to compositions comprising non-micronized otic agents. In some instances, the micronized otic agent (e.g., ciprofloxacin) provides a steady supply (e.g., +/−20%) of active agent via slow degradation and serves as a depot for the active agent; such a depot effect increases residence time of the otic agent in the ear. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

In some embodiments, the viscosity of any formulation described herein is designed to provide a suitable rate of release from an auris compatible gel. In some embodiments, the concentration of a thickening agent (e.g., gelling components such as polyoxyethylene-polyoxypropylene copolymers) allows for a tunable mean dissolution time (MDT). The MDT is inversely proportional to the release rate of an active agent from a composition or device described herein. Experimentally, the released otic agent is optionally fitted to the Korsmeyer-Peppas equation $$\frac{Q}{Q_\alpha} = kt^n + b$$

where Q is the amount of otic agent released at time t, $Q\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is optionally calculated by:

$$MDT = \frac{nk^{-1/n}}{n+1}$$

For example, a linear relationship between the mean dissolution time (MDT) of a composition or device and the concentration of the gelling agent (e.g., poloxamer) indicates that the otic agent is released due to the erosion of the polymer gel (e.g., poloxamer) and not via diffusion. In another example, a non-linear relationship indicates release of otic agent via a combination of diffusion and/or polymer gel degradation. In another example, a faster gel elimination time course of a composition or device (a faster release of active agent) indicates lower mean dissolution time (MDT). The concentration of gelling components and/or active agent in a composition are tested to determine suitable parameters for MDT. In some embodiments, injection volumes are also tested to determine suitable parameters for preclinical and clinical studies. The gel strength and concentration of the active agent affects release kinetics of an otic agent from the composition. At low poloxamer concentration, elimination rate is accelerated (MDT is lower). An increase in otic agent concentration in the composition or device prolongs residence time and/or MDT of the otic agent in the ear.

In some embodiments, the MDT for poloxamer from a composition or device described herein is at least 6 hours. In some embodiments, the MDT for poloxamer from a composition or device described herein is at least 10 hours.

In some embodiments, the MDT for an active agent from a composition or device described herein is from about 30 hours to about 48 hours. In some embodiments, the MDT for an active agent from a composition or device described herein is from about 30 hours to about 96 hours. In some embodiments, the MDT for an active agent from a composition or device described herein is from about 30 hours to about 1 week. In some embodiments, the MDT for a composition or device described herein is from about 1 week to about 6 weeks.

In some embodiments, the mean residence time (MRT) for an active agent in a composition or device described herein is from about 20 hours to about 48 hours. In some embodiments, the MRT for an active agent from a composition or device described herein is from about 20 hours to about 96 hours. In some embodiments, the MRT for an active agent from a composition or device described herein is from about 20 hours to about 1 week.

In some embodiments, the MRT for an active agent is about 20 hours. In some embodiments, the MRT for an active agent is about 30 hours. In some embodiments, the MRT for an active agent is about 40 hours. In some embodiments, the MRT for an active agent is about 50 hours. In some embodiments, the MRT for an active agent is about 60 hours. In some embodiments, the MRT for an active agent is about 70 hours. In some embodiments, the MRT for an active agent is about 80 hours. In some embodiments, the MRT for an active agent is about 90 hours. In some embodiments, the MRT for an active agent is about 1 week. In some embodiments, the MRT for an active agent is about 90 hours. In some embodiments, the MRT for a composition or device described herein is from about 1 week to about 6 weeks. In some embodiments, the MRT for an active agent is about 1 week. In some embodiments, the MRT for an active agent is about 2 weeks. In some embodiments, the MRT for an active agent is about 3 weeks. In some embodiments, the MRT for an active agent is about 4 weeks. In some embodiments, the MRT for an active agent is about 5 weeks. The half life of an otic agent and mean residence time of the otic agent are determined for each formulation by measurement of concentration of the otic agent in the EAC using procedures described herein.

In some embodiments, the use of a composition comprising micronized ciprofloxacin described herein for the treatment of middle ear effusion provides a middle ear MRT of 150 to 300 h. In some embodiments, the use of a composition comprising micronized ciprofloxacin described herein for the treatment of middle ear effusion provides a middle ear MRT of 175 to 275 h. In some embodiments, the use of a composition comprising micronized ciprofloxacin described herein for the treatment of middle ear effusion provides a middle ear MRT of 200 to 250 h. In some embodiments, the use of a composition comprising micronized ciprofloxacin described herein for the treatment of middle ear effusion provides a middle ear MRT of 160 to 190 h. In some embodiments, the use of a composition comprising micronized ciprofloxacin described herein for the treatment of middle ear effusion provides a middle ear MRT of 170 to 180 h. In some embodiments, the use of a composition comprising micronized ciprofloxacin described herein for the treatment of middle ear effusion provides a middle ear MRT of 250 to 300 h. In some embodiments, the use of a composition comprising micronized ciprofloxacin described herein for the treatment of middle ear effusion provides a middle ear MRT of 265 to 285 h. In some embodiments, the use of a composition comprising micronized ciprofloxacin described herein for the treatment of middle ear effusion provides a middle ear MRT of about 175 h, about 180 h, about 185 h, about 190 h, about 195 h, about 200 h, about 210 h, about 220 h, about 225 h, about 230 h, about 240 h, about 250 h, about 260 h, about 270 h, or about 275 h.

In certain embodiments, any controlled release otic formulation described herein increases the exposure of an otic agent and increases the Area Under the Curve (AUC) in otic fluids (e.g., EAC) by about 30%, about 40%, about 50%, about 60%, about 70%, about 80% or about 90% compared to a formulation that is not a controlled release otic formulation.

In certain embodiments, any controlled release otic formulation described herein increases the exposure time of an otic agent and decreases the Cmax in otic fluids (e.g., EAC) by about 40%, about 30%, about 20%, or about 10%, compared to a formulation that is not a controlled release otic formulation. In certain embodiments, any controlled release otic formulation described herein alters (e.g. reduces) the ratio of Cmax to Cmin compared to a formulation that is not a controlled release otic formulation. In certain embodiments, any controlled release otic formulation described herein increases the exposure of an otic agent and increases the length of time that the concentration of an otic agent is above Cmin by about 30%, about 40%, about 50%, about 60%, about 70%, about 80% or about 90% compared to a formulation that is not a controlled release otic formulation. In certain instances, controlled release formulations described herein delay the time to Cmax. In certain instances, the controlled steady release of a drug prolongs the time the concentration of the drug will stay above the Cmin. In some embodiments, auris compositions described herein prolong the residence time of a drug in the outer ear and provide a stable drug exposure profile. In some instances, an increase in concentration of an active agent in the composition saturates the clearance process and allows for a more rapid and stable steady state to be reached.

In some embodiments, the use of a composition comprising micronized ciprofloxacin described herein for the treatment of middle ear effusion provides exposure to high and stable ciprofloxacin concentrations in the middle ear compartment. In some embodiments, the use of a composition comprising micronized ciprofloxacin described herein for the treatment of middle ear effusion provides a middle ear ciprofloxacin $C_{max}$ of 50 to 125 µg/mL. In some embodiments, the use of a composition comprising micronized ciprofloxacin described herein for the treatment of middle ear effusion provides a middle ear ciprofloxacin $C_{max}$ of 75 to 100 µg/mL. In some embodiments, the use of a composition comprising micronized ciprofloxacin described herein for the treatment of middle ear effusion provides a middle ear ciprofloxacin $C_{max}$ of about 75 µg/mL, about 80 µg/mL, about 85 µg/mL, about 90 µg/mL, about 95 µg/mL, or about 100 µg/mL. In some embodiments, the use of a composition comprising micronized ciprofloxacin described herein for the treatment of middle ear effusion provides a middle ear ciprofloxacin $C_{max}$ of at least 50 µg/mL, at least 75 µg/mL, at least 80 µg/mL, at least 85 µg/mL, at least 90 µg/mL, at least 95 µg/mL, or at least 100 µg/mL. In some embodiments, the use of a composition comprising micronized ciprofloxacin described herein for the treatment of middle ear effusion provides a middle ear ciprofloxacin $C_{max}$ of at least 50 µg/mL. In some embodiments, the use of a composition comprising micronized ciprofloxacin described herein for the treatment of middle ear effusion provides a middle ear ciprofloxacin $C_{max}$ of at least 60 µg/mL. In some embodiments, the use of a composition comprising micronized ciprofloxacin described herein for the treatment of middle ear effusion provides a middle ear ciprofloxacin $C_{max}$ of at least 75 µg/mL.

In some embodiments, the use of a composition comprising micronized ciprofloxacin described herein for the treatment of outer ear effusion provides an outer ear ciprofloxacin AUC of 7,500 to 50,000 µg·h/mL. In certain embodiments, the use of a composition comprising micronized ciprofloxacin described herein for the treatment of outer ear effusion provides an outer ear ciprofloxacin AUC of 10,000 to 25,000 µg·h/mL. In certain embodiments, the use of a composition comprising micronized ciprofloxacin described herein for the treatment of outer ear effusion provides an outer ear ciprofloxacin AUC of about 10,000 µg·h/mL, 12,000 µg·h/mL, about 15,000 µg·h/mL, about 17,000 µg·h/mL, about 20,000 µg·h/mL, about 22,000 µg·h/mL, or about 25,000 µg·h/mL. In certain embodiments, the use of a composition comprising micronized ciprofloxacin described herein for the treatment of outer ear effusion provides an outer ear ciprofloxacin AUC of about 10,000 µg·h/mL. In certain embodiments, the use of a composition comprising micronized ciprofloxacin described herein for the treatment of outer ear effusion provides an outer ear ciprofloxacin AUC of about 15,000 µg·h/mL. In certain embodiments, the use of a composition comprising micronized ciprofloxacin described herein for the treatment of outer ear effusion provides an outer ear ciprofloxacin AUC of about 17,000 µg·h/mL. In certain embodiments, the use of a composition comprising micronized ciprofloxacin described herein for the treatment of outer ear effusion provides an outer ear ciprofloxacin AUC of about 20,000 µg·h/mL. In certain embodiments, the use of a composition comprising micronized ciprofloxacin described herein for the treatment of outer ear effusion provides an outer ear ciprofloxacin AUC of about 25,000 µg·h/mL.

In some embodiments, the use of a composition comprising micronized ciprofloxacin described herein for the treatment of outer ear effusion provides an outer ear ciprofloxacin $AUC_{0-24}$ of 1,000 to 3,000 µg·h/mL. In certain embodiments, the use of a composition comprising micronized ciprofloxacin described herein for the treatment of outer ear effusion provides an outer ear ciprofloxacin $AUC_{0-24}$ of 2,000 to 2,500 µg·h/mL. In certain embodiments, the use of a composition comprising micronized ciprofloxacin described herein for the treatment of outer ear effusion provides an outer ear ciprofloxacin $AUC_{0-24}$ of about 1,000 µg·h/mL, 1,200 µg·h/mL, about 1,400 µg·h/mL, about 1,600 µg·h/mL, about 1,800 µg·h/mL, about 2,000 µg·h/mL, about 2,100 µg·h/mL, about 2,200 µg·h/mL, about 2,300 µg·h/mL, about 2,400 µg·h/mL, about 2,500 µg·h/mL, about 2,600 µg·h/mL, about 2,700 µg·h/mL, about 2,800 µg·h/mL, or about 3,000 µg·h/mL. In certain embodiments, the use of a composition comprising micronized ciprofloxacin described herein for the treatment of outer ear effusion provides an outer ear ciprofloxacin $AUC_{0-24}$ of about 2,000 µg·h/mL. In certain embodiments, the use of a composition comprising micronized ciprofloxacin described herein for the treatment of outer ear effusion provides an outer ear ciprofloxacin $AUC_{0-24}$ of about 2,100 µg·h/mL. In certain embodiments, the use of a composition comprising micronized ciprofloxacin described herein for the treatment of outer ear effusion provides an outer ear ciprofloxacin $AUC_{0-24}$ of about 2,200 μg·h/mL. In certain embodiments, the use of a composition comprising micronized ciprofloxacin described herein for the treatment of outer ear effusion provides an outer ear ciprofloxacin $AUC_{0-24}$ of about 2,300 μg·h/mL. In certain embodiments, the use of a composition comprising micronized ciprofloxacin described herein for the treatment of outer ear effusion provides an outer ear ciprofloxacin $AUC_{0-24}$ of about 2,400 μg·h/mL. In certain embodiments, the use of a composition comprising micronized ciprofloxacin described herein for the treatment of outer ear effusion provides an outer ear ciprofloxacin $AUC_{0-24}$ of about 2,500 μg·h/mL.

In some embodiments, the use of a composition comprising micronized ciprofloxacin described herein for the treatment of outer ear effusion provides an outer ear ciprofloxacin T>MIC (time of ciprofloxacin above minimum inhibitory concentration) of about 350 to 800 h. In some embodiments, the use of a composition comprising micronized ciprofloxacin described herein for the treatment of outer ear effusion provides an outer ear ciprofloxacin T>MIC of about 400 to 730 h. In some embodiments, the use of a composition comprising micronized ciprofloxacin described herein for the treatment of outer ear effusion provides an outer ear ciprofloxacin T>MIC of about 400 h, about 425 h, about 450 h, about 475 h, about 500 h, about 525 h, about 550 h, about 575 h, about 600 h, about 625 h, about 650 h, about 675 h, about 700 h, about 725 h, or about 730 h. In some embodiments, the use of a composition comprising micronized ciprofloxacin described herein for the treatment of outer ear effusion provides an outer ear ciprofloxacin T>MIC of about 450 h. In some embodiments, the use of a composition comprising micronized ciprofloxacin described herein for the treatment of outer ear effusion provides an outer ear ciprofloxacin T>MIC of about 500 h. In some embodiments, the use of a composition comprising micronized ciprofloxacin described herein for the treatment of outer ear effusion provides an outer ear ciprofloxacin T>MIC of about 550 h. In some embodiments, the use of a composition comprising micronized ciprofloxacin described herein for the treatment of outer ear effusion provides an outer ear ciprofloxacin T>MIC of about 600 h. In some embodiments, the use of a composition comprising micronized ciprofloxacin described herein for the treatment of outer ear effusion provides an outer ear ciprofloxacin T>MIC of about 650 h.

In some embodiments, the use of a composition comprising micronized ciprofloxacin described herein for the treatment of outer ear effusion provides a middle ear ciprofloxacin $C_{max}$/MIC (minimum inhibitory concentration) ratio of 40 to 50. In some embodiments, the use of a composition comprising micronized ciprofloxacin described herein for the treatment of outer ear effusion provides an outer ear ciprofloxacin $C_{max}$/MIC ratio of about 40. In some embodiments, the use of a composition comprising micronized ciprofloxacin described herein for the treatment of outer ear effusion provides an outer ear ciprofloxacin $C_{max}$/MIC ratio of about 42. In some embodiments, the use of a composition comprising micronized ciprofloxacin described herein for the treatment of outer ear effusion provides an outer ear ciprofloxacin $C_{max}$/MIC ratio of about 44. In some embodiments, the use of a composition comprising micronized ciprofloxacin described herein for the treatment of outer ear effusion provides an outer ear ciprofloxacin $C_{max}$/MIC ratio of about 46. In some embodiments, the use of a composition comprising micronized ciprofloxacin described herein for the treatment of outer ear effusion provides an outer ear ciprofloxacin $C_{max}$/MIC ratio of about 48. In some embodiments, the use of a composition comprising micronized ciprofloxacin described herein for the treatment of outer ear effusion provides an outer ear ciprofloxacin $C_{max}$/MIC ratio of about 50. In some embodiments, the use of a composition comprising micronized ciprofloxacin described herein for the treatment of outer ear effusion provides an outer ear ciprofloxacin $C_{max}$/MIC (minimum inhibitory concentration) ratio of at least 10. In some embodiments, the use of a composition comprising micronized ciprofloxacin described herein for the treatment of outer ear effusion provides an outer ear ciprofloxacin $C_{max}$/MIC (minimum inhibitory concentration) ratio of at least 20. In some embodiments, the use of a composition comprising micronized ciprofloxacin described herein for the treatment of outer ear effusion provides an outer ear ciprofloxacin $C_{max}$/MIC (minimum inhibitory concentration) ratio of at least 30. In some embodiments, the use of a composition comprising micronized ciprofloxacin described herein for the treatment of outer ear effusion provides an outer ear ciprofloxacin $C_{max}$/MIC (minimum inhibitory concentration) ratio of at least 40.

In some embodiments, the use of a composition comprising micronized ciprofloxacin described herein for the treatment of outer ear effusion provides an outer ear ciprofloxacin $AUC_{0-24}$/MIC (minimum inhibitory concentration) ratio of 1000 to 1200. In some embodiments, the use of a composition comprising micronized ciprofloxacin described herein for the treatment of outer ear effusion provides an outer ear ciprofloxacin $AUC_{0-24}$/MIC ratio of about 900. In some embodiments, the use of a composition comprising micronized ciprofloxacin described herein for the treatment of outer ear effusion provides an outer ear ciprofloxacin $AUC_{0-24}$/MIC ratio of about 1000. In some embodiments, the use of a composition comprising micronized ciprofloxacin described herein for the treatment of outer ear effusion provides an outer ear ciprofloxacin $AUC_{0-24}$/MIC ratio of about 1050. In some embodiments, the use of a composition comprising micronized ciprofloxacin described herein for the treatment of outer ear effusion provides an outer ear ciprofloxacin $AUC_{0-24}$/MIC ratio of about 1100. In some embodiments, the use of a composition comprising micronized ciprofloxacin described herein for the treatment of outer ear effusion provides an outer ear ciprofloxacin $AUC_{0-24}$/MIC ratio of about 1150. In some embodiments, the use of a composition comprising micronized ciprofloxacin described herein for the treatment of outer ear effusion provides an outer ear ciprofloxacin $AUC_{0-24}$/MIC ratio of about 1200. In some embodiments, the use of a composition comprising micronized ciprofloxacin described herein for the treatment of outer ear effusion provides an outer ear ciprofloxacin $AUC_{0-24}$/MIC (minimum inhibitory concentration) ratio of at least 100. In some embodiments, the use of a composition comprising micronized ciprofloxacin described herein for the treatment of outer ear effusion provides an outer ear ciprofloxacin $AUC_{0-24}$/MIC (minimum inhibitory concentration) ratio of at least 250. In some embodiments, the use of a composition comprising micronized ciprofloxacin described herein for the treatment of outer ear effusion provides an outer ear ciprofloxacin $AUC_{0-24}$/MIC (minimum inhibitory concentration) ratio of at least 500. In some embodiments, the use of a composition comprising micronized ciprofloxacin described herein for the treatment of outer ear effusion provides an outer ear ciprofloxacin $AUC_{0-24}$/MIC (minimum inhibitory concentration) ratio of at least 1000.

In certain instances, once drug exposure (e.g., concentration in the EAC) of a drug reaches steady state, the concentration of the drug in the EAC stays at or about the therapeutic dose for an extended period of time (e.g., one day, 2 days, 3 days, 4 days, 5 days, 6 days, or 1 week, 3 weeks, 6 weeks, 2 months). In some embodiments, the steady state concentration of active agent released from a controlled release formulation described herein is about 5 to about 20 times the steady state concentration of an active agent released from a formulation that is not a controlled release formulation. In some embodiments, the steady state concentration of active agent released from a controlled release formulation described herein is about 20 to about 50 times the steady state concentration of an active agent released from a formulation that is not a controlled release formulation.

Controlled Release Formulations

In general, controlled release drug formulations impart control over the release of drug with respect to site of release and time of release within the body. As discussed herein, controlled release refers to immediate release, delayed release, sustained release, extended release, variable release, pulsatile release and bi-modal release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Auris Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

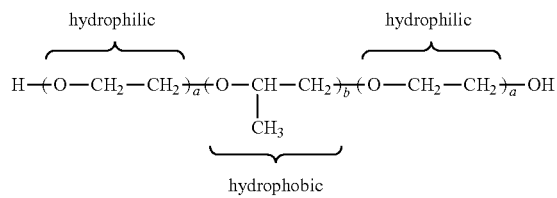

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong etal, Nature (1997), 388:860-2; Jeong etal, J. Control. Release (2000), 63:155-63; Jeong etal, Adv. Drug Delivery Rev. (2002), 54:37-51).

The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

REGEL® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include ATRIGEL® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The antimicrobial agent and various additives such as buffers, salts, and preservatives are subsequently added and dissolved. In some instances the antimicrobial agent and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as CARBOPOL® 934P, to the composition (Majithiya etal, AAPS PharmSciTech (2006), 7(3), p. E1; EP0551626, both of which is incorporated herein by reference for such disclosure).

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising an antimicrobial agent and a pharmaceutically acceptable buffer. In another embodiment, the pharmaceutically acceptable excipient or carrier is a gelling agent.

In other embodiments, useful antimicrobial agent auris-acceptable pharmaceutical formulations also include one or more pH adjusting agents or buffering agents to provide an EAC suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris externa's natural buffering system. In some embodiments, from about 10 µM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are aqueous thermoreversible gel formulations comprising an antimicrobial agent and a thermoreversible polymer, such as a poloxamer (e.g. Poloxamer 407). In some embodiments, the concentration of the thermoreversible polymer in the water being sufficient to provide a final viscosity (after intratympanic injection) from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP.

In some embodiments, the viscosity of the gel formulations presented herein is measured by any means described. For example, in some embodiments, an LVDV-II+CP Cone Plate Viscometer and a Cone Spindle CPE-40 are used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

Also described herein are controlled release formulations comprising an otic agent and a viscosity enhancing agent. Suitable viscosity-enhancing agents include by way of example only, gelling agents and suspending agents. By way of example only, the auris-acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, CARBOPOL®, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), SPLENDA® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the otic agents disclosed herein acts as a controlled release formulation, restricting the diffusion of the otic agents from the formulation. Moreover, the combination of carboxymethylated chitosan and alginate is optionally used to assist in increasing the permeability of the otic agents through the skin of the EAC.

If desired, the auris-acceptable pharmaceutical gels also contain osmolality adjustors and other excipients in addition, buffering agents, and pH adjusting agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at about 7.0 to about 8.0. In some embodiments, the buffering agent (e.g. tromethamine) is included at a concentration of about 0.4% to about 0.6% on a weight basis of the total composition.

In some embodiments, the composition further comprises one or more EAC protectant, including exocrine gland secreted agents disclosed herein. In some embodiments, the EAC protectant is selected from squalene, lanosterol, and cholesterol. In some embodiments, the EAC protectant is one or more antimicrobial agent. In some embodiments, the antimicrobial agent is an antimicrobial peptide.

General Methods of Sterilization

Provided herein are otic compositions that ameliorate or lessen otic disorders described herein. Further provided herein are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing," which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave. In some embodiments, the formulations described herein comprise micronized antimicrobial agents (e.g., micronized ciprofloxacin) that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C.: Health Industry Manufacturers Association, 1981) and involve challenging the membrane filter with a known quantity (ca. $10^7/cm^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., ciprofloxacin) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In some instances, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma irradiation, filtration) lead to degradation of polymeric components (e.g., thermosetting, gelling or mucoadhesive polymer components) and/or the active agent in the formulation. In some instances, sterilization of an auris formulation by filtration through membranes (e.g., 0.2 µM membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the EAC.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of E. coli LPS. Humans can develop a response to as little as 5 EU/kg of body weight. The bioburden (e.g., microbial limit) and/or sterility (e.g., endotoxin level) is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP) <71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

Methods of Treatment
Dosing Methods and Schedules

Provided herein are methods of administering therapeutic formulations disclosed herein to the outer ear. In some embodiments, the methods comprise administering the formulation with a dropper, bulb, tube, syringe, or any other appropriate tube having an orifice for dispensing the formulation. In some embodiments, the methods comprise administering the formulation with a syringe. In some embodiments, the syringe comprises a cylindrical syringe body wherein the body is compartmentalized in that each compartment is able to store at least one component of the auris-acceptable antimicrobial agent gel formulation. In a further embodiment, the syringe having a compartmentalized body allows for mixing of the components prior to application to the aurus externa. In other embodiments, the delivery system comprises multiple syringes, each syringe of the multiple syringes contains at least one component of the gel formulation such that each component is pre-mixed prior administration. In a further embodiment, the syringes disclosed herein comprise at least one reservoir wherein the at least one reservoir comprises an antimicrobial agent, or a pharmaceutically acceptable buffer, or a viscosity enhancing agent, such as a gelling agent or a combination thereof. Commercially available syringes may be employed in their simplest form as ready-to-use plastic syringes with a syringe barrel, plunger with a plunger rod, and holding flange, to perform administration.

In some embodiments, the methods do not require a needle with the syringe, as the formulation is only applied to the aurus externa, which is readily accessible with they syringe alone. In some embodiments, the therapeutic formulation is administered with a syringe and needle. In some embodiments, the delivery system is a syringe and needle apparatus that is capable of unloading the otic compositions or formulations disclosed herein onto the surface of the tympanic membrane or into the external auditory canal. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the otic agent compositions or formulations, the gauge level of the syringe or hypodermic needle may be varied accordingly. In another embodiment, the internal diameter of the needle can be increased by reducing the wall thickness of the needle (commonly referred as thin wall or extra thin wall needles) to reduce the possibility of needle clogging while maintaining an adequate needle gauge. In some embodiments, the needle is a needle used for instant delivery of the gel formulation. The needle may be a single use needle or a disposable needle. In some embodiments, a syringe may be used for delivery of the pharmaceutically acceptable gel-based otic agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized.

In some embodiments, the compositions described herein are administered in a volume that contains about 1 mg to about 50 mg, from about 1 mg to about 40 mg, from about 1 mg to about 30 mg, from about 5 mg to about 25 mg, from about 6 mg to about 24 mg, from about 8 mg to about 18 mg, from about 10 mg to about 15 mg, or from about 11 mg to about 13 mg of an antimicrobial agent disclosed herein.

In some embodiments, the compositions described herein are administered in a volume that contains about 1 mg to about 50 mg of ciprofloxacin, from about 1 mg to about 40 mg, from about 1 mg to about 30 mg of ciprofloxacin, from about 5 mg to about 25 mg of ciprofloxacin, from about 6 mg to about 24 mg of ciprofloxacin, from about 8 mg to about 18 mg of ciprofloxacin, from about 10 mg to about 15 mg of ciprofloxacin, or from about 11 mg to about 13 mg of ciprofloxacin disclosed herein. In some embodiments, the compositions described herein are administered in a volume that contains about 6 mg of ciprofloxacin. In some embodiments, the compositions described herein are administered in a volume that contains about 8 mg of ciprofloxacin. In some embodiments, the compositions described herein are administered in a volume that contains about 10 mg of ciprofloxacin. In some embodiments, the compositions described herein are administered in a volume that contains about 12 mg of ciprofloxacin. In some embodiments, the compositions described herein are administered in a volume that contains about 14 mg of ciprofloxacin. In some embodiments, the compositions described herein are administered in a volume that contains about 16 mg of ciprofloxacin. In some embodiments, the compositions described herein are administered in a volume that contains about 18 mg of ciprofloxacin. In some embodiments, the compositions described herein are administered in a volume that contains about 20 mg of ciprofloxacin.

In some embodiments, the compositions described herein are administered in a volume of about 0.1 mL to about 1 mL. In some embodiments, the compositions described herein are administered in a volume of about 0.2 mL to about 1 mL. In some embodiments, the compositions described herein are administered in a volume of about 0.1 mL to about 0.8 mL. In some embodiments, the compositions described herein are administered in a volume of about 0.2 mL. In some embodiments, the compositions described herein are administered in a volume of about 0.4 mL. In some embodiments, the compositions described herein are administered in a volume of about 0.6 mL. In some embodiments, the compositions described herein are administered in a volume of about 0.8 mL.

In some embodiments, the compositions described herein are administered in a volume of about 0.1 mL to about 0.5 mL that contains about 1 mg of ciprofloxacin to about 30 mg ciprofloxiacin. In some embodiments, the compositions described herein are administered in a volume of about 0.1 mL to about 0.5 mL that contains about 5 mg of ciprofloxacin to about 25 mg ciprofloxiacin. In some embodiments, the compositions described herein are administered in a volume of about 0.1 mL to about 0.5 mL that contains about 10 mg of ciprofloxacin to about 15 mg ciprofloxiacin. In some embodiments, the compositions described herein are administered in a volume of about 0.4 mL that contains about 1 mg of ciprofloxacin to about 30 mg ciprofloxiacin. In some embodiments, the compositions described herein are administered in a volume of about 0.4 mL that contains about 10 mg of ciprofloxacin to about 15 mg ciprofloxiacin. In some embodiments, the compositions described herein are administered in a volume of about 0.3 mL to about 0.5 mL that contains about 10 mg of ciprofloxacin to about 15 mg ciprofloxiacin. In some embodiments, the compositions described herein are administered in a volume of about 0.1 mL that contains about 6 mg of ciprofloxacin. In some embodiments, the compositions described herein are administered in a volume of about 0.2 mL that contains about 12 mg of ciprofloxacin. In some embodiments, the compositions described herein are administered in a volume of about 0.4 mL that contains about 24 mg of ciprofloxacin.

In some embodiments, those dosages are in the form of a composition comprising 15-17% by weight of poloxamer 407 and 5.4-6.6% by weight of micronized ciprofloxacin. In some embodiments, those dosages are in the form of a composition comprising 15-17% by weight of poloxamer 407 and 1.8-2.2% by weight of micronized ciprofloxacin.

The auris-acceptable compositions or formulations containing the antimicrobial agent compound(s) described herein may be administered for prophylactic and/or therapeutic treatments. In therapeutic applications, the antimicrobial agent compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

Frequency of Administration

In some embodiments, a composition disclosed herein is administered to an individual in need thereof once. In some embodiments, a composition disclosed herein is administered to a subject in a single injection to the patient's infected ear. In some embodiments, a composition disclosed herein is administered to an individual in need thereof more than once.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an antimicrobial may be administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the antimicrobial agent compounds may be administered chronically, that is, for an extended period of time, including throughout the duration of the patient's life in order to ameliorate or otherwise control or limit the symptoms of the patient's disease or condition.

The amount of antimicrobial agent that will correspond to such an amount will vary depending upon factors such as the particular compound, disease condition and its severity, according to the particular circumstances surrounding the case, including, e.g., the specific antimicrobial agent being administered, the route of administration, the autoimmune condition being treated, the target area being treated, and the subject or host being treated.

Pharmacokinetics of Controlled Release Formulations

In some embodiments, the formulation provides an extended/sustained release formulation of at least one antimicrobial agent. In certain embodiments, diffusion of at least one antimicrobial agent from the formulation occurs for a time period exceeding 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one antimicrobial agent is released from the formulation for a time period exceeding 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In a specific embodiment the formulation provides a therapeutically effective amount of at least one antimicrobial agent at the site of disease with essentially no systemic exposure. In an additional embodiment the formulation provides a therapeutically effective amount of at least one antimicrobial agent at the site of disease with essentially no detectable systemic exposure. In other embodiments, the formulation provides a therapeutically effective amount of at least one antimicrobial agent at the site of disease with little or no detectable detectable systemic exposure.

The combination of immediate release, delayed release and/or extended release antimicrobial agent compositions or formulations may be combined with other pharmaceutical agents, as well as the excipients, diluents, stabilizers, tonicity agents and other components disclosed herein. As such, depending upon the antimicrobial agent used, the thickness or viscosity desired, or the mode of delivery chosen, alternative aspects of the embodiments disclosed herein are combined with the immediate release, delayed release and/or extended release embodiments accordingly.

Kits/Articles of Manufacture

The disclosure also provides kits for preventing, treating or ameliorating the symptoms of a disease or disorder in a mammal. Such kits generally will comprise one or more of the antimicrobial agent controlled-release compositions or devices disclosed herein, and instructions for using the kit. The disclosure also contemplates the use of one or more of the antimicrobial agent controlled-release compositions, in the manufacture of medicaments for treating, abating, reducing, or ameliorating the symptoms of a disease, dysfunction, or disorder in a mammal, such as a human that has, is suspected of having, or at risk for developing an outer ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of antimicrobial agent formulations compositions provided herein are contemplated as are a variety of treatments for any disease, disorder, or condition that would benefit by controlled release administration of an antimicrobial agent to the outer ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Summary of a Study to Assess Ciprofloxacin Treatment of Otitis Externa This study evaluated the clinical feasibility, efficacy and safety of administering a single dose of a 6% ciprofloxacin otic suspension (referred to as OTO-201) to the external auditory canal (EAC) in an office-based setting in 75 patients presenting with otitis externa. Three dose volumes (0.1, 0.2, and 0.4 mL [6-24 mg]) of the ciprofloxacin formulation was evaluated. Patients were monitored for 28 days, and main outcome measures were feasibility (deliverability), clinical cure, as judged by erythema/edema/otalgia composite score, and safety (otoscopy, adverse events).

The recommended administration procedure for delivery was as follows:
1. Thoroughly irrigate and/or suction EAC of otorrhea and/or debris.
2. Using a 1 mL luer-lock syringe, direct 0.1, 0.2 or 0.4 mL of OTO-201 to the EAC using a blunt tipped syringe.
3. Advance the syringe tip medially approximately 5 mm beyond the cartilaginous/bony junction and inject OTO-201 slowly onto EAC. Record any observations of OTO-201 that exudes laterally from the EAC.

Figure 2:
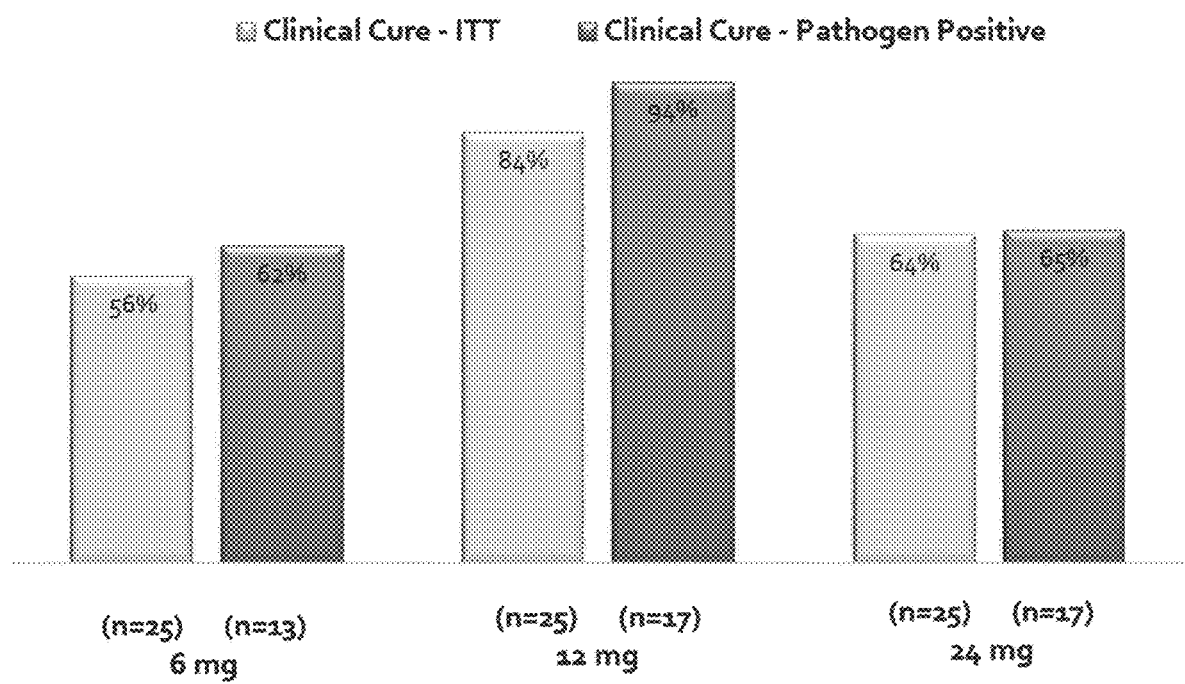
FIG. 2 shows a clinical cure analysis of treatment with various doses of a 6% Ciprofloxacin otic suspension. Clinical cure is defined as having a subjective score of 0 for erythema, edema, otorrhea and otalgia on a 0-3 rating scale for each symptom.

Trial results showed that the ciprofloxacin formulation was easily administered to the EAC in all patients. Evaluation at Day 15 demonstrated a 62-84% clinical cure rate in the intent-to-treat group, depending on the dose, and a 62-94% clinical cure rate in the pathogen positive patient subset. Presumed bacterial eradication ranged from 71-100%. Administration of the ciprofloxacin formulation was well-tolerated. Interestingly, the 12 mg (0.2 mL) dose was more effective than the 24 mg (0.4 mL) dose (see FIG. 2).

This Phase 2 clinical trial demonstrated that a single administration of different dose volumes of the ciprofloxacin formulation to the EAC was feasible in an office-based setting and was associated with acceptable clinical and bacterial cure rates. The study supports the advancement of 0.2 mL dose of the ciprofloxacin formulation to Phase 3 study as a potential new treatment for otitis externa.

Example 2—A 1-Month, Prospective, Multicenter, Open-Label Study of OTO-201 Given as a Single Administration for Treatment of Otitis Externa A 1-month, multicenter, open-label study was performed in which eligible subjects with unilateral otitis externa (OE) were randomized to receive a single external auditory canal (EAC) administration of one of three dose volumes of OTO-201 to the affected ear. The study was designed to evaluate the feasibility of administering different dose volumes of OTO-201 to the EAC in patients with OE, to evaluate the safety and feasibility of EAC administration of OTO-201 in subjects with OE, and to assess the clinical activity of OTO-201 in subjects with OE.

Once a subject met all eligibility criteria, they were randomized to one of three cohorts, 6 mg OTO-201 (0.1 mL dose volume), 12 mg OTO-201 (0.2 mL dose volume) or 24 mg OTO-201 (0.4 mL dose volume). Baseline cultures of EAC fluids were taken on all subjects. Each cohort was comprised of approximately 25 subjects. After unilateral EAC administration of OTO-201 to the affected ear on Day 1 (Visit 1), subjects were entered in a 4-week follow-up period. Subjects returned to study sites on Days 4, 8, 15 and 29 to assess safety and clinical activity of OTO-201, or upon early withdrawal from the study. Day 15 was defined as the Test of Cure Visit (clinical cure, defined as complete resolution of signs and symptoms with no further requirement for antimicrobial therapy). At each study, visit signs and symptoms were recorded using the following scale:
 a. Signs: edema, erythema and otorrhea
 b. Symptoms: otalgia and tenderness
 c. Scoring scale:
  0=none (complete absence of any signs or symptoms)
  1=mild (slight)
  2=moderate (definitely present)
  3=severe (marked, intense)

During Days 1 through 15, subjects or their caregivers reported symptoms of otalgia in the affected ear in a daily diary using the Wong-Baker FACES® Pain Rating Scale of 0 to 10 where 0=no hurt and 10=hurts worst. Each subject recorded the date at which the study ear pain ended. Daily diary was completed only in subjects mature enough to provide appropriate responses to level of otalgia, typically 3 years or older.

For any subject that that showed no improvement by the Test of Cure Visit, or subject diaries indicated no improvement in otalgia, those subjects were determined treatment failures and were provided standard of care.

The duration of the study for each subject was approximately 1 month.

Diagnosis and Main Criteria for Inclusion:

Subjects meeting all of the following criteria may be eligible for the study:
1. Subject is a male or female aged 6 months to 80 years, inclusive
2. Subject has a clinical diagnosis of unilateral otitis externa
3. Subject or subject's caregiver is willing to comply with the protocol and attend all study visits
4. Subject or subject's caregiver is able to provide written informed consent and Health Insurance Portability and Accountability Act (HIPAA) documents before the initiation of any study-related procedures
5. Female subjects of childbearing potential (i.e., not surgically sterile and/or not post-menopausal (≥12 months since last menstrual period and 45 years of age or older)) must have a negative pregnancy test before randomization. Women of childbearing potential who are not abstinent from sex with male partners may be entered into the study if they are using and willing to continue to use adequate contraceptive precautions for the duration of the study (e.g., oral contraceptives, contraceptive implant or injection, intrauterine device, condom and spermicide, or diaphragm and spermicide).
6. Subject of appropriate age is able to provide assent for participation in the study Diagnosis and Main Criteria for Exclusion:

Subjects meeting any of the following criteria are not eligible for participation:
1. Subject has tympanic membrane perforation
2. Subject has severe OE that either includes auricular cellulitis or chrondritis or prevents administration of OTO-201
3. Subject has fungal OE, based on clinical signs
4. Subject has a history of known immunodeficiency disease
5. Presence of any infection requiring systemic antimicrobial or antifungal agents 6. Subject has used ear drops of any kind to the affected ear within 1 week of screening.
7. Subject has a history of allergy to ciprofloxacin or any of the components of OTO-201
8. Subject has any other clinically significant illness or medical condition that, in the opinion of either the investigator or medical monitor, would prohibit the subject from participating in the study
9. Subject has used an investigational drug or device in the month prior to screening
10. Subject has been previously exposed to OTO-201
11. Subject is pregnant or lactating.

Test Product, Dose and Mode of Administration:
Subjects randomized will receive one of the following doses of OTO-201:
- 6 mg OTO-201, single 0.1 mL administration to the EAC to the affected ear
- 12 mg OTO-201, single 0.2 mL administration to the EAC to the affected ear
- 24 mg OTO-201, single 0.4 mL administration to the EAC to the affected ear OTO-201 was supplied in one vial (60 mg/mL OTO-201 Drug Product). Each subject will be given 6, 12 or 24 mg OTO-201 to the EAC of the study ear via administration. OTO-201 Drug Product is a sterile suspension in a 2.0 mL single-patient-use glass vial. All kits containing OTO-201 were stored at 2-8° C., with allowable temperature excursions within 0 to 40° C. for up to 72 hours. All temperature excursions of OTO-201 were documented in the study drug accountability records. Any excursions within the allowable temperature range and conditions were documented, but OTO-201 was still acceptable for use and dispensing to subjects. If any excursions were outside of these conditions, OTO-201 were not used to treat subjects. If this occurred, the site immediately contacted the Sponsor to designate that the kit was unacceptable for dispensing so it can be removed from inventory.

The OTO-201 syringes were prepared according to instructions.

The instructions for preparation of OTO-201 are provided in the Site Operations Manual. Each dose of OTO-201 will be given as a single administration to the EAC of the affected ear. The recommended administration procedure for delivery of OTO-201 is as follows:
1. Thoroughly irrigate and/or suction EAC of otorrhea and/or debris.
2. Using a 1 mL luer-lock syringe, direct 0.1, 0.2 or 0.4 mL of OTO-201 to the EAC using a blunt tipped syringe.
3. Advance the syringe tip medially approximately 5 mm beyond the cartilaginous/bony junction and inject OTO-201 slowly onto EAC. Record any observations of OTO-201 that exudes laterally from the EAC.

Duration of treatment was a single unilateral administration to the EAC on Day 1.

Concomitant use of the following medications was prohibited:
Antibiotics other than (a) OTO-201 or (b) topical dermal antibiotics for abrasions (see Note below)
Ear drops of any kind (see Note below)
Over the counter topical agents, such as acetic acid, or devices indicated for the treatment of swimmer's ear
Other investigational drug(s) or device(s)
Antibiotics other than OTO-201 that are deemed necessary for the welfare of the subject during the study are not prohibited. The type of antibiotic, dose, and duration of treatment should be recorded. If OTO-201 is not able to be given, or if new onset otitis externa or the continuation of OE is present 7 days post-administration in the treated ear, the subject should be treated per standard of care (SOC). If the subject had a clinical diagnosis of unilateral OE and the unaffected ear develops OE during the course of the study, the unaffected ear should be treated per SOC.

Safety assessments included consideration of adverse events (AEs), otoscopic examinations, concomitant medications, vital signs, feasibility of administration to the EAC.

Clinical activity assessments included consideration of signs and symptoms rating scale and subject otalgia diaries and time to resolution.

The following assessments were performed at Visit 1.
Before Administration:
Informed consent
Confirm eligibility criteria
Urine pregnancy test (for female subjects aged 9 years or older)
Medical history
Physical examination
Height and weight measurements
Vital Signs
Otoscopic examination
Microbiology culture
Concomitant medications
Randomization to OTO-201 dose
OTO-201 administration
After Administration:
Feasibility of OTO-201 administration to the EAC
Provide subject/caregiver instructions on daily diary reporting
Adverse events
The following assessments were performed at Study Visits 2, 3 & 4.
Otoscopic examination
Review daily diary reporting
Microbiology culture (only if otorrhea is present)
Concomitant medications
Adverse events
The following assessments were performed at Study Visit 5.
Vital signs
Weight measurements
Urine pregnancy test (for female subjects aged 9 years or older)
Otoscopic examination
Microbiology culture (only if otorrhea is present)
Concomitant medications
Adverse events
Clinical activity assessments were assessed by:
Signs and Symptoms of OE
Otoscopic exams will be used to assess the signs and symptoms of OE at every study visit using the following scale:
Signs: edema, erythema and otorrhea
Symptoms: otalgia and tenderness
Scoring scale:
0=none (complete absence of any signs or symptoms)
1=mild (slight)
2=moderate (definitely present)
3=severe (marked, intense)
Daily diary on otalgia and time to resolution
Safety data was summarized by count and percentage for event and categorical data (e.g., adverse events, EAC feasibility). Continuous outcomes (e.g., vital signs) were summarized with N, mean, standard deviation, minimum, maximum, median, and interquartile range. Change from baseline included 95% confidence intervals. Safety will be assessed by dose level and overall.

Feasibility of the procedure was assessed on Day 1 by the treating physician. These data were tabulated by number (N) and percentage. The feasibility analysis was conducted using the Safety Analysis Set.

The safety analysis was conducted using the Safety Analysis Set defined as all subjects who receive at least one OTO-201 administration. Safety assessments through Day 29 included treatment emergent AEs, SAEs, and changes from baseline with respect to otoscopic, and concomitant medications. Adverse events were coded according to the Medical Dictionary for Regulatory Activities (MedDRA) and were summarized by system organ class and preferred term. Concomitant medications were classified according to World Health Organization Drug Dictionary (WHO Drug) and were summarized by drug class and preferred drug name. Change from baseline also included a 95% confidence interval. Categorical variables, not specifically mentioned above were summarized by N and percentage at each visit recorded. Similarly, continuous measures were summarized by N, mean, standard deviation, minimum, maximum, interquartile range, and median. Change from baseline included a 95% confidence interval.

The clinical activity analysis was conducted using the intent to treat (ITT) and per protocol (PP) analysis populations. Analyses based on the ITT population were considered to be primary.

All summaries of results were proved separately by dose and overall. Although statistical testing was performed among the three dose levels, no hypotheses were made. Analyses was performed using SAS version 9.3 or later.

Clinical activity was determined at the otoscopic exams and with clinical cure being the complete resolution of signs and symptoms with no further use of antimicrobial therapy.

Time to cessation of edema, erythema, otorrhea, otalgia and tenderness through Visit 4 was described with the use of Kaplan-Meier plots. The three dose groups was compared with log-rank tests. If at least half of the ears in a given treatment group had a cessation (a value of zero, in the absence of prohibited medications) of the outcome being assessed, the median time and its 95% confidence interval was provided. Use of prohibited medication resulted in censoring at that point in the Kaplan-Meier analysis. The N and percentage of ears with cessation for each sign and symptom and the percentage of subjects demonstrating a cessation was presented.

In addition to time to event analyses, analysis of covariate (ANCOVA) was used to analyze each sign and symptom. The best (lowest) score and the average score after treatment through visit 4 was analyzed, using the baseline score as a covariate. Similar analyses were conducted with the Wong-Baker FACES® Pain Rating Scale. The average and best score was analyzed with ANCOVA, with the baseline measure used as a covariate.

The primary analysis was conducted using the ITT analysis population; analysis with the PP population was secondary.

The time and events schedule for this study is shown in Table 1.

TABLE 1

Time and Events Schedule

| Procedure | Screening/ OTO-201 Administration Visit 1 Day 1 | Follow-up Visit 2 Day 4 + 1 day | Follow-up Visit 3 Day 8 ± 2 days | Follow-up Visit 4 Day 15 ± 2 days | End-of-Study/Early Termination Visit 5[a] Day 29 ± 3 days | Unscheduled Visit Unscheduled N/A |
|---|---|---|---|---|---|---|
| Informed consent and HIPAA documents | X | | | | | |
| Eligibility criteria | X | | | | | |
| Medical history[b] | X | | | | | |
| Physical examination | X | | | | | |
| Vital signs[c] | X | | | | X | |
| Height and weight measurements | X | | | | X[d] | |
| Pregnancy test[e] | X | | | | X | |
| Otoscopic examination | X | X | X | X | X | X |
| Microbiology culture[f] | X | X[g] | X[g] | X[g] | X[g] | |
| Randomization | X | | | | | |
| OTO-201 Administration | X | | | | | |
| Feasibility of EAC Administration | X | | | | | |
| Instruct/review diary requirements[h] | X | X | X | X | | |
| Concomitant medications | X | X | X | X | X | X |
| Adverse event monitoring[i] | X | X | X | X | X | X |

[a]Procedures scheduled for Visit 5 were performed at the end of study visit or upon early discontinuation from the study.
[b]Medical history included information on demographics.
[c]Vital sign measurements included blood pressure, pulse rate and temperature.
[d]Only weight measured at Visit 5.
[e]Urine pregnancy testing was conducted on all female subjects aged 9 years or older at Visit 1 and 5. Pregnancy testing was conducted and confirmed negative prior study drug administration on Visit 1. If a subject was found to be pregnant after dosing with study drug, they should complete the follow-up period.
[f]All samples were shipped to a central lab for analysis. A specimen for culture was taken prior to OTO-201 administration.
[g]Culture performed only if otorrhea is present in the EAC.
[h]Daily diary completed only in subjects mature enough to provide appropriate responses to level of otalgia, typically 3 years or older.
[i]Adverse event information was collected from the time of OTO-201 administration until study termination for all subjects randomized.

The following defines the analytic sample for the relevant endpoints used in particular analyses.

Safety Analysis Set: The safety analysis set included all subjects who receive study drug. Subjects were analyzed as treated.

Intent to Treat (ITT) Analysis Set: The ITT analysis set included all subjects who were randomized. Subjects were analyzed as randomized. Clinical activity was assessed in this analysis population.

Per Protocol (PP): The PP analysis set included all ITT subjects who received study drug and complete Visit 4 and who did not have a major protocol deviation. Subjects were analyzed as treated. Clinical activity was assessed in this analysis population and was secondary to and supportive of the ITT analysis.

The analysis included a descriptive statistics or tabulations for each questionnaire item in order to assess the feasibility of EAC administration.

I claim:

1. A method of treating otitis externa or a sign or symptom thereof, comprising administering into an external ear canal of a subject in need thereof, an aqueous thermoreversible gel composition,
   wherein:
   the composition comprises about 6.0% by weight of micronized ciprofloxacin and 15-17% by weight of poloxamer 407,
   the dose volume of the composition administered to the subject comprises about 12 mg of micronized ciprofloxacin, and
   the dose volume of the thermoreversible gel composition administered to the subject is about 0.2 mL.

2. The method of claim 1, wherein the composition is free of butylated hydroxytoluene (BHT).

3. The method of claim 1, wherein the composition is preservative-free.

4. The method claim 1, wherein the composition further comprises tromethamine.

5. The method of claim 1, wherein the composition has a pH of about 7.0 to about 8.0.

6. The method of claim 1, wherein the otitis externa is associated with a bacterial infection.

7. The method of claim 6, wherein the bacterial infection is associated with *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof.

8. The method of claim 1, wherein otitis externa is acute otitis externa.

9. The method of claim 1, wherein the subject has experienced a symptom of acute otitis externa for less than six weeks, wherein the symptom is selected from decreased hearing, swelling of the ear canal, ear pain, fever, exudate from the ear canal, itching, redness, and combinations thereof.

10. The method of claim 1, wherein administering comprises contacting the ear canal with a tip of a syringe containing the aqueous thermoreversible gel composition.

11. The method of claim 10, wherein the tip of the syringe is advanced about 1 mm to about 8 mm beyond the cartilaginous/bony junction of the ear.

12. The method of claim 10, wherein the tip of the syringe is advanced about 5 mm beyond the cartilaginous/bony junction of the ear.

13. The method of claim 1, wherein the composition further comprises hydrochloric acid.

14. The method of claim 1, wherein the composition comprises about 0.4% to about 0.6% tromethamine by weight.

15. The method of claim 1, wherein the sign or symptom is edema, erythema, otorrhea, otalgia, temporary conductive hearing loss, shedding of the ear canal, redness of the ear canal, lack of cerumen, pain of the outer ear, external acoustic meatus inflammation with or without infection, itching, aural fullness, tenderness of the tragus and pinna, diffuse ear canal edema, conductive hearing loss or combinations thereof.

16. The method of claim 8, wherein the otitis externa is associated with intermediate and resistant bacterial strains to ciprofloxacin.

17. The method of claim 8, wherein there is onset of the sign or symptom of otitis externa within 48 hours.

* * * * *